United States Patent
Lange

(10) Patent No.: US 11,407,796 B2
(45) Date of Patent: Aug. 9, 2022

(54) ANTISECRETORY FACTOR 17

(71) Applicant: LANTMÄNNEN AS-FAKTOR AB, Stockholm (SE)

(72) Inventor: Stefan Lange, Gothenburg (SE)

(73) Assignee: LANTMÄNNEN AS-FAKTOR AB, Stockholm (SE)

(*) Notice: Subject to any disclaimer, the term of this patent is extended or adjusted under 35 U.S.C. 154(b) by 0 days.

(21) Appl. No.: 16/318,419

(22) PCT Filed: Jul. 18, 2017

(86) PCT No.: PCT/EP2017/068111
§ 371 (c)(1),
(2) Date: Jan. 17, 2019

(87) PCT Pub. No.: WO2018/015379
PCT Pub. Date: Jan. 25, 2018

(65) Prior Publication Data
US 2019/0345210 A1 Nov. 14, 2019

(30) Foreign Application Priority Data
Jul. 18, 2016 (SE) .................................. 1651074-5

(51) Int. Cl.
*C07K 14/47* (2006.01)
*A61K 38/00* (2006.01)

(52) U.S. Cl.
CPC .......... *C07K 14/4703* (2013.01); *A61K 38/00* (2013.01)

(58) Field of Classification Search
None
See application file for complete search history.

(56) References Cited

U.S. PATENT DOCUMENTS

| | | |
|---|---|---|
| 2011/0305773 A1 | 12/2011 | Hansson et al. |
| 2012/0093716 A1 | 4/2012 | Jennische et al. |
| 2019/0192622 A1 | 6/2019 | Hansson |

FOREIGN PATENT DOCUMENTS

| | | |
|---|---|---|
| CN | 102387811 A | 3/2012 |
| CN | 104689299 A | 6/2015 |
| CN | 105025916 A | 11/2015 |
| WO | WO97/08202 A1 | 3/1997 |
| WO | WO2005/030246 A1 | 4/2005 |
| WO | WO2007/126363 A2 | 11/2007 |
| WO | WO2010/093324 A1 | 8/2010 |
| WO | WO2014/096384 A1 | 6/2014 |
| WO | WO2015/157283 A1 | 10/2015 |
| WO | WO2015/181324 A1 | 12/2015 |

OTHER PUBLICATIONS

Dombkowski et al. (Protein disulfide engineering; FEBS Letters 588 (2014) 206-212).*
Bende, N. S., et al., "The insecticidal neurotoxin Aps III is an atypical knottin peptide that potently blocks insect voltage-gated sodium channels," Biochem. Pharmacol. 2013;85(10):31 pp.
Nicolas, V., et al., "Antisecretory Factor Peptide AF-16 Inhibits the Secreted Autotransporter Toxin-Stimulated Transcellular and Paracellular Passages of Fluid in Cultured Human Enterocyte-Like Cells," Infection and Immunity 2015;83(3) 907-922.
International Search Report and Written Opinion for PCT Patent App. No. PCT/EP2017/068111 (dated Oct. 2, 2017).
Johansson, E., et al., "Identification of an active site in the antisecretory factor protein," Biochimica et Biophysica Acta 1997;1362:177-182.
Lange, S., et al., "The Antisecretory Factor: Synthesis, Anatomical and Cellular Distribution and Biological Action in Experimental and Clinical Studies," Int. Rev. Cytol. 2011;210:39-75.
Al-Olama, M., et al., "Uptake of the antisecretory factor peptide AF-16 in rat blood and cerebrospinal fluid and effects on elevated intracranial pressure," Acta. Neurochir. 2015;157:129-137.
Muttenthaler, M., et al., "Modulating Oxytocin Activity and Plasma Stability by Disulfide Bond Engineering," J. Med. Chem. 2010;53:8585-8596.
King, G. F., "Venoms as a platform for human drugs: translating toxins into therapeutics," Expert Opin. Biol. Ther. 2011;11(11):1469-1484.
King, G. F., et al., "Spider-Venom Peptides: Structure, Pharmacology, and Potential for Control of Insect Pests," Ann. Rev. Entomol. 2013;58:475-496.
Lauer-Fields, J. L., et al., "Application of Topologically Constrained Mini-Proteins as Ligands, Substrates, and Inhibitors," Methods in Mol. Biol. 2007;386:125-166.
Li, Y., et al., "Disulfide bond prolongs the half-life of therapeutic peptide-GLP-1," Peptides 2011;32:1400-1407.
Li, Y., et al., "GLP-1 analogs containing disulfide bond exhibited prolonged half-life in vivo than GLP-1," Peptides 2011;32:1303-1312.
Schmoldt, H. U., et al., "A fusion protein system for the recombinant production of short disulfide bond rich cystine knot peptides using barnase as a purification handle," Protein Expr. Purif. 2005;39(1):82-89, Abstract only.
Sikora, K., et al., "The Role of Counter-Ions in Peptides—An Overview," Pharmaceuticals 2020, vol. 13, No. 442, 29 pp.
Jennische, E., et al., "The peptide AF-16 abolishes sickness and death at experimental encephalitis by reducing increase of intracranial pressure," Brain Res. 2008;1227:189-197.

(Continued)

*Primary Examiner* — James H Alstrum-Acevedo
*Assistant Examiner* — Tara L Martinez
(74) *Attorney, Agent, or Firm* — Cermak Nakajima & McGowan LLP; Malcolm K. McGowan

(57) ABSTRACT

The present invention relates to a new peptide called Antisecretory Factor (AF) 17 which is an isolated recombinant and/or synthetically produced which has a t½ of at least 1.8 h. The peptide is e.g. useful for normalizing pathological fluid transport and/or inflammatory reactions in animals and in humans. AF-17 and pharmaceutical compositions of AF-17 can e.g. be used for treating and/or preventing TBI and/or secondary brain injuries associated with TBI, as well as for treating and/or preventing acquired brain injuries and to optimize cancer treatment.

11 Claims, 19 Drawing Sheets

Figure 1:
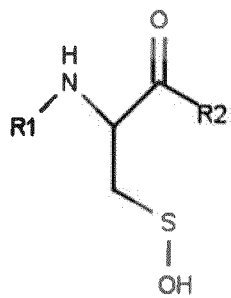
Figure 1:
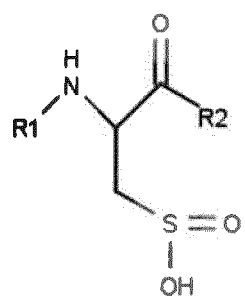
Figure 1:
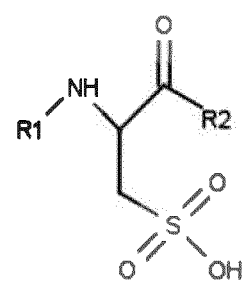

Specification includes a Sequence Listing.

(56) References Cited

OTHER PUBLICATIONS

Li, S., et al., "The application and prospect of antisecretory factor (AF)," Heilongjiang Science 2015;6(2):pp. 14-15 and 41.
Notification of First Office Action for Chinese Patent App. No. 201780044967.1 (dated Sep. 2, 2021) with English language translation thereof.

\* cited by examiner

SEQUENCE LISTING

```
<160> NUMBER OF SEQ ID NOS: 20

<210> SEQ ID NO 1
<211> LENGTH: 382
<212> TYPE: PRT
<213> ORGANISM: Homo sapiens
<220> FEATURE:
<223> OTHER INFORMATION: FULL-LENGTH

<400> SEQUENCE: 1

Met Val Leu Glu Ser Thr Met Val Cys Val Asp Asn Ser Glu Tyr Met
1               5                   10                  15

Arg Asn Gly Asp Phe Leu Pro Thr Arg Leu Gln Ala Gln Gln Asp Ala
            20                  25                  30

Val Asn Ile Val Cys His Ser Lys Thr Arg Ser Asn Pro Glu Asn Asn
        35                  40                  45

Val Gly Leu Ile Thr Leu Ala Asn Asp Cys Glu Val Leu Thr Thr Leu
    50                  55                  60

Thr Pro Asp Thr Gly Arg Ile Leu Ser Lys Leu His Thr Val Gln Pro
65                  70                  75                  80

Lys Gly Lys Ile Thr Phe Cys Thr Gly Ile Arg Val Ala His Leu Ala
                85                  90                  95

Leu Lys His Arg Gln Gly Lys Asn His Lys Met Arg Ile Ile Ala Phe
            100                 105                 110

Val Gly Ser Pro Val Glu Asp Asn Glu Lys Asp Leu Val Lys Leu Ala
        115                 120                 125

Lys Arg Leu Lys Lys Glu Lys Val Asn Val Asp Ile Ile Asn Phe Gly
    130                 135                 140

Glu Glu Glu Val Asn Thr Glu Lys Leu Thr Ala Phe Val Asn Thr Leu
145                 150                 155                 160

Asn Gly Lys Asp Gly Thr Gly Ser His Leu Val Thr Val Pro Pro Gly
                165                 170                 175

Pro Ser Leu Ala Asp Ala Leu Ile Ser Ser Pro Ile Leu Ala Gly Glu
            180                 185                 190

Gly Gly Ala Met Leu Gly Leu Gly Ala Ser Asp Phe Glu Phe Gly Val
        195                 200                 205

Asp Pro Ser Ala Asp Pro Glu Leu Ala Leu Ala Leu Arg Val Ser Met
    210                 215                 220

Glu Glu Gln Arg His Ala Gly Gly Gly Ala Arg Arg Ala Arg Ala
225                 230                 235                 240

Ser Ala Ala Glu Ala Gly Ile Ala Thr Thr Gly Thr Glu Asp Ser Asp
                245                 250                 255

Asp Ala Leu Leu Lys Met Thr Ile Ser Gln Gln Glu Phe Gly Arg Thr
            260                 265                 270

Gly Leu Pro Asp Leu Ser Ser Met Thr Glu Glu Glu Gln Ile Ala Tyr
        275                 280                 285
```

```
Ala Met Gln Met Ser Leu Gln Gly Ala Glu Phe Gly Gln Ala Glu Ser
    290                 295                 300

Ala Asp Ile Asp Ala Ser Ser Ala Met Asp Thr Ser Glu Pro Ala Lys
305                 310                 315                 320

Glu Glu Asp Asp Tyr Asp Val Met Gln Asp Pro Glu Phe Leu Gln Ser
                325                 330                 335

Val Leu Glu Asn Leu Pro Gly Val Asp Pro Asn Asn Glu Ala Ile Arg
            340                 345                 350

Asn Ala Met Gly Ser Leu Pro Pro Arg Pro Arg Thr Ala Arg Arg
        355                 360                 365

Thr Arg Arg Arg Lys Thr Arg Ser Glu Thr Gly Lys Gly
    370                 375                 380

<210> SEQ ID NO 2
<211> LENGTH: 6
<212> TYPE: PRT
<213> ORGANISM: Homo sapiens
<220> FEATURE:
<223> OTHER INFORMATION: PEPTIDE
<220> FEATURE:
<221> NAME/KEY: VARIANT
<222> LOCATION: 2
<223> OTHER INFORMATION: may be replaced by R or K
<220> FEATURE:
<221> NAME/KEY: VARIANT
<222> LOCATION: 3
<223> OTHER INFORMATION: may be replaced by L
<220> FEATURE:
<221> NAME/KEY: VARIANT
<222> LOCATION: 5
<223> OTHER INFORMATION: may be replaced by A

<400> SEQUENCE: 2

Cys His Ser Lys Thr Arg
1               5

<210> SEQ ID NO 3
<211> LENGTH: 16
<212> TYPE: PRT
<213> ORGANISM: Homo sapiens
<220> FEATURE:
<223> OTHER INFORMATION: PEPTIDE
<220> FEATURE:
<221> NAME/KEY: VARIANT
<222> LOCATION: 3
<223> OTHER INFORMATION: may be replaced with R or K
<220> FEATURE:
<221> NAME/KEY: VARIANT
<222> LOCATION: 4
<223> OTHER INFORMATION: may be replaced with L
<220> FEATURE:
<221> NAME/KEY: VARIANT
<222> LOCATION: 6
<223> OTHER INFORMATION: may be replaced with A

<400> SEQUENCE: 3

Val Cys His Ser Lys Thr Arg Ser Asn Pro Glu Asn Asn Val Gly Leu
1               5                   10                  15

<210> SEQ ID NO 4
<211> LENGTH: 7
<212> TYPE: PRT
<213> ORGANISM: Homo sapiens
<220> FEATURE:
<223> OTHER INFORMATION: PEPTIDE
<220> FEATURE:
<221> NAME/KEY: VARIANT
<222> LOCATION: 3
```

```
<223> OTHER INFORMATION: may be replaced by R or K
<220> FEATURE:
<221> NAME/KEY: VARIANT
<222> LOCATION: 4
<223> OTHER INFORMATION: may be replaced by L
<220> FEATURE:
<221> NAME/KEY: VARIANT
<222> LOCATION: 6
<223> OTHER INFORMATION: may be replaced by A

<400> SEQUENCE: 4

Val Cys His Ser Lys Thr Arg
1               5

<210> SEQ ID NO 5
<211> LENGTH: 8
<212> TYPE: PRT
<213> ORGANISM: Homo sapiens
<220> FEATURE:
<223> OTHER INFORMATION: PEPTIDE
<220> FEATURE:
<221> NAME/KEY: VARIANT
<222> LOCATION: 4
<223> OTHER INFORMATION: may be replaced by R or K
<220> FEATURE:
<221> NAME/KEY: VARIANT
<222> LOCATION: 5
<223> OTHER INFORMATION: may be replaced by L
<220> FEATURE:
<221> NAME/KEY: VARIANT
<222> LOCATION: 7
<223> OTHER INFORMATION: may be replaced by A

<400> SEQUENCE: 5

Ile Val Cys His Ser Lys Thr Arg
1               5

<210> SEQ ID NO 6
<211> LENGTH: 5
<212> TYPE: PRT
<213> ORGANISM: Homo sapiens
<220> FEATURE:
<223> OTHER INFORMATION: PEPTIDE
<220> FEATURE:
<221> NAME/KEY: VARIANT
<222> LOCATION: 1
<223> OTHER INFORMATION: may be replaced by R or K
<220> FEATURE:
<221> NAME/KEY: VARIANT
<222> LOCATION: 2
<223> OTHER INFORMATION: may be replaced by L
<220> FEATURE:
<221> NAME/KEY: VARIANT
<222> LOCATION: 4
<223> OTHER INFORMATION: may be replaced by A

<400> SEQUENCE: 6

His Ser Lys Thr Arg
1               5

<210> SEQ ID NO 7
<211> LENGTH: 16
<212> TYPE: PRT
<213> ORGANISM: Artificial Sequence
<220> FEATURE:
<223> OTHER INFORMATION: PEPTIDE
<220> FEATURE:
<221> NAME/KEY: VARIANT
<222> LOCATION: 3
<223> OTHER INFORMATION: may be replaced with R or K
<220> FEATURE:
<221> NAME/KEY: VARIANT
<222> LOCATION: 4
```

```
<223> OTHER INFORMATION: may be replaced with L
<220> FEATURE:
<221> NAME/KEY: VARIANT
<222> LOCATION: 6
<223> OTHER INFORMATION: may be replaced with A

<400> SEQUENCE: 7

Val Cys His Ser Lys Thr Arg Ser Asn Pro Glu Asn Asn Val Gly Leu
1               5                   10                  15

<210> SEQ ID NO 8
<211> LENGTH: 6
<212> TYPE: PRT
<213> ORGANISM: Artificial Sequence
<220> FEATURE:
<223> OTHER INFORMATION: PEPTIDE
<220> FEATURE:
<221> NAME/KEY: VARIANT
<222> LOCATION: 2
<223> OTHER INFORMATION: may be replaced by R or K
<220> FEATURE:
<221> NAME/KEY: VARIANT
<222> LOCATION: 3
<223> OTHER INFORMATION: may be replaced by L
<220> FEATURE:
<221> NAME/KEY: VARIANT
<222> LOCATION: 5
<223> OTHER INFORMATION: may be replaced by A

<400> SEQUENCE: 8

Cys His Ser Lys Thr Arg
1               5

<210> SEQ ID NO 9
<211> LENGTH: 7
<212> TYPE: PRT
<213> ORGANISM: Artificial Sequence
<220> FEATURE:
<223> OTHER INFORMATION: DISULFIDE at Cys in position 2
<220> FEATURE:
<221> NAME/KEY: VARIANT
<222> LOCATION: 3
<223> OTHER INFORMATION: may be replaced by R or K
<220> FEATURE:
<221> NAME/KEY: VARIANT
<222> LOCATION: 4
<223> OTHER INFORMATION: may be replaced by L
<220> FEATURE:
<221> NAME/KEY: VARIANT
<222> LOCATION: 6
<223> OTHER INFORMATION: may be replaced by A

<400> SEQUENCE: 9

Val Cys His Ser Lys Thr Arg
1               5

<210> SEQ ID NO 10
<211> LENGTH: 11
<212> TYPE: PRT
<213> ORGANISM: Artificial Sequence
<220> FEATURE:
<223> OTHER INFORMATION: PEPTIDE

<400> SEQUENCE: 10

Thr Arg Ser Asn Pro Glu Asn Asn Val Gly Leu
1               5                   10

<210> SEQ ID NO 11
<211> LENGTH: 6
<212> TYPE: PRT
<213> ORGANISM: Artificial Sequence
```

```
<220> FEATURE:
<223> OTHER INFORMATION: PEPTIDE

<400> SEQUENCE: 11

Glu Asn Asn Val Gly Leu
1               5

<210> SEQ ID NO 12
<211> LENGTH: 14
<212> TYPE: PRT
<213> ORGANISM: Artificial Sequence
<220> FEATURE:
<223> OTHER INFORMATION: PEPTIDE

<400> SEQUENCE: 12

His Ser Lys Thr Arg Ser Asn Pro Glu Asn Asn Val Gly Leu
1               5                   10

<210> SEQ ID NO 13
<211> LENGTH: 4
<212> TYPE: PRT
<213> ORGANISM: Artificial Sequence
<220> FEATURE:
<223> OTHER INFORMATION: PEPTIDE

<400> SEQUENCE: 13

Asn Val Gly Leu
1

<210> SEQ ID NO 14
<211> LENGTH: 9
<212> TYPE: PRT
<213> ORGANISM: Artificial Sequence
<220> FEATURE:
<223> OTHER INFORMATION: PEPTIDE

<400> SEQUENCE: 14

Ser Asn Pro Glu Asn Asn Val Gly Leu
1               5

<210> SEQ ID NO 15
<211> LENGTH: 10
<212> TYPE: PRT
<213> ORGANISM: Artificial Sequence
<220> FEATURE:
<223> OTHER INFORMATION: PEPTIDE

<400> SEQUENCE: 15

Val Cys His Ser Lys Thr Arg Ser Asn Pro
1               5                   10

<210> SEQ ID NO 16
<211> LENGTH: 15
<212> TYPE: PRT
<213> ORGANISM: Artificial Sequence
<220> FEATURE:
<223> OTHER INFORMATION: PEPTIDE

<400> SEQUENCE: 16

Cys His Ser Lys Thr Arg Ser Asn Pro Glu Asn Asn Val Gly Leu
1               5                   10                  15

<210> SEQ ID NO 17
<211> LENGTH: 13
<212> TYPE: PRT
<213> ORGANISM: Artificial Sequence
<220> FEATURE:
```

```
<223> OTHER INFORMATION: PEPTIDE

<400> SEQUENCE: 17

Ser Lys Thr Arg Ser Asn Pro Glu Asn Asn Val Gly Leu
1               5                   10

<210> SEQ ID NO 18
<211> LENGTH: 10
<212> TYPE: PRT
<213> ORGANISM: Artificial Sequence
<220> FEATURE:
<223> OTHER INFORMATION: PEPTIDE

<400> SEQUENCE: 18

Arg Ser Asn Pro Glu Asn Asn Val Gly Leu
1               5                   10

<210> SEQ ID NO 19
<211> LENGTH: 8
<212> TYPE: PRT
<213> ORGANISM: Artificial Sequence
<220> FEATURE:
<223> OTHER INFORMATION: PEPTIDE

<400> SEQUENCE: 19

Asn Pro Glu Asn Asn Val Gly Leu
1               5

<210> SEQ ID NO 20
<211> LENGTH: 6
<212> TYPE: PRT
<213> ORGANISM: Artificial Sequence
<220> FEATURE:
<223> OTHER INFORMATION: PEPTIDE

<400> SEQUENCE: 20

Glu Asn Asn Val Gly Leu
1               5
```

ANTISECRETORY FACTOR 17

CROSS-REFERENCE TO RELATED APPLICATIONS

This application is a National Stage Entry of PCT/EP2017/068111, filed Jul. 18, 2017, which claims priority from Swedish patent application 1651074-5, filed Jul. 18, 2016. The contents of these priority applications are incorporated herein by reference in their entirety.

FIELD OF INVENTION

Antisecretory factor (AF) is a protein complex which inhibits inflammation and regulates fluid-transport; the AF complex resides in modified proteasomes. Synthetic peptides, comprising the antidiarrhoeic sequence AF-16, located between the amino acid positions 35 and 50 on the antisecretory factor (AF) protein sequence, have prior been characterized (WO 97/08202; WO 05/030246). AF16 is known to be rapidly degrading in plasma. The present invention discloses AF-16's major metabolic fate in plasma, which is a rapid disulfide formation of AF16, resulting in AF-16 comprising a cysteine disulfide at amino acid position 2 (C2) (hereinafter called AF-17). This action, being reversible, clearly protects AF16 from rapid peptidase degradation. Based on this surprising insight, the present invention for the first time discloses synthetic peptides, comprising AF-17, which, when administered to a patient in need thereof, provide a substantially prolonged half-life of AF16.

BACKGROUND OF THE INVENTION

Antisecretory Factor (AF)

Antisecretory factor (AF) is a 41 kDa protein that originally was described to provide protection against diarrhea diseases and intestinal inflammation (for a review, see: The antisecretory factor: synthesis, anatomical and cellular distribution, and biological action in experimental and clinical studies. Int Rev Cytol, 2001. 210: p. 39-75.). The antisecretory factor (AF) protein has been sequenced and its cDNA cloned. The antisecretory activity seems to be mainly exerted by a peptide located between the amino acid positions 35 and 50 on the antisecretory factor (AF) protein sequence (i.e. the antidiarrhoeic sequence/consensus sequence) comprising at least 4-16, such as in particular 4, 6, 7, 8 or 16 amino acids of the antidiarrhoeic sequence. Immunochemical and immunohistochemical investigations have revealed that the antisecretory factor (AF) protein is present and may also be synthesized by most tissues and organs in a body. Synthetic peptides, comprising the antidiarrhoeic/consensus sequence or fragments thereof, have prior been characterized (WO 97/08202; WO 05/030246). Antisecretory factor (AF) proteins and peptides have previously been disclosed to normalize pathological fluid transport and/or inflammatory reactions, such as in the intestine and the choroid plexus in the central nervous system after challenge with cholera toxin (WO 97/08202). Food and feed with the capacity to either induce endogenous synthesis of AF or uptake of added AF have therefore been suggested to be useful for the treatment of edema, diarrhea, dehydration and inflammation e.g. in WO 97/08202. WO 98/21978 discloses the use of products having enzymatic activity for the production of a food that induces the formation of antisecretory factor (AF) proteins. WO 00/038535 further discloses food products enriched in native antisecretory factor (AF) proteins as such (NASP).

Antisecretory factor (AF) proteins and fragments thereof have also been shown to improve the repair of nervous tissue, and proliferation, apoptosis, differentiation, and/or migration of stem and progenitor cells and cells derived thereof in the treatment of conditions associated with loss and/or gain of cells (WO 05/030246) and to be equally effective in the treatment and/or prevention of intraocular hypertension (WO 07/126364), as for the treatment and/or prevention of compartment syndrome (WO 07/126363).

The present inventors have further shown that AF is able to monitor and/or beneficially affect the structure, distribution and multiple functions of lipid rafts, receptors and/or caveolae in membranes and thus to be useful for the treatment and/or prevention of structural disorganization and dysfunction of lipid rafts and/or caveolae in cell membranes (WO 07/126365).

The present inventors have further been able to prove that the same antisecretory factor (AF) protein, as well as peptides and fragments thereof, can intervene in the biological activation of transmembrane proteins, e.g. NKCC1 through FAK and CAP, and that it can thus directly regulate the pathological activity of the ion channel in pathological and/or perturbed cells, effectively normalizing the intracellular pressure and transmembrane protein function in said cell, and thus allowing an improved uptake of drugs used in e.g. cancer therapy (WO 2010/093324).

The present inventors isolated a protein named AF1 (antisecretory factor 1) from blood, and sequenced its encoding gene. Later, AF1 was shown to be a constituent of the 19S proteasome subunit, and as such named PSMD4, RPN10 or S5a. It was further shown that bacterial enterotoxins and processed cereals were able to induce an altered form of antisecretory factor (AF), which inhibited inflammation and fluid secretion in the gut. This modified form of AF was found to bind to the polysaccharide agarose. After elution with α-methylglucoside, its concentration could be determined by ELISA.

Surprisingly, it was recently demonstrated that proteasomes react with the complement factors C3 after intake of processed cereals (SPC). This reaction results in exposure of previously hidden antisecretory epitopes, and the proteasome/complement complex formation results in the splitting of C3 into its inactive form C3c.

Accordingly, there are many medical conditions which would benefit from the administration of AF-16. Unfortunately, it has been shown to have a very short half-life in the body of the patients once administered.

The present invention for the first time presents an isolated, recombinant, or synthetically produced protected AF16 metabolite (herein referred to as AF-17), with a substantially prolonged half-life in the body of the patients once administered.

SUMMARY OF THE PRESENT INVENTION

In one embodiment, the present invention relates to an isolated recombinant and/or synthetically produced peptide, hereinafter referred to as AF-17 (as shown in SEQ.ID.NO. 7), or a pharmaceutically active salt thereof, having equivalent functional activity, which comprises an amino acid sequence as shown in SEQ.ID.NO. 3 (AF-16) and a cysteine disulfide in amino acid position no. 2 of SEQ.ID.NO. 3, said peptide having antisecretory activity.

Figure 12:
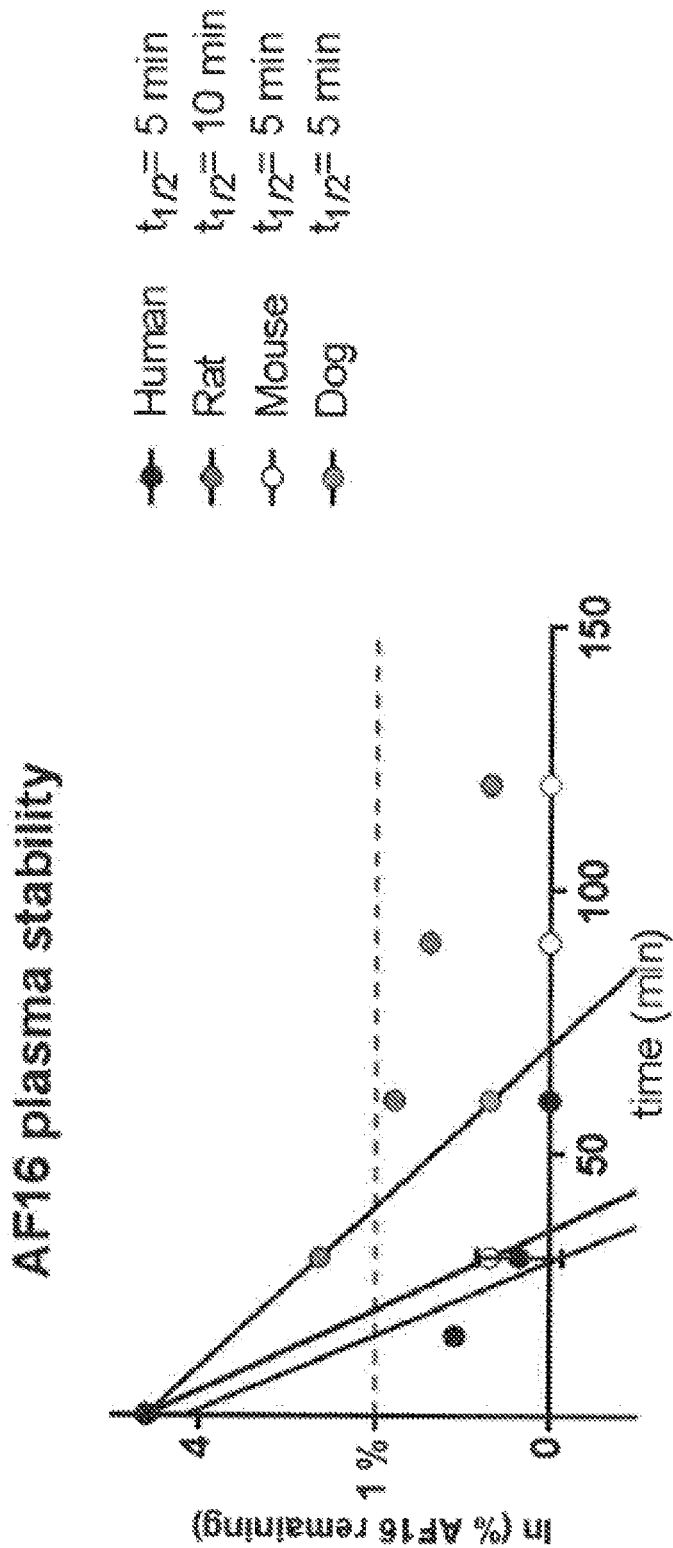

The relative stability of AF16 in different species is shown in FIG. 12. As is for the first time documented herein, irrespective of species, AF16 is rapidly disappearing, with an in vitro half-life ($t_{1/2}$) less than or equal to 10 min. The present inventors were furthermore for the first time able to determine the molecular fate of the peptide AF-16 after administration, leading to a thorough understanding of the pharmacokinetic basis of any pharmacological action of AF and to the development of a new AF-peptide (AF-17) with improved in vitro half-life ($t_{1/2}$), enabling improved means for monitoring the fate of the active AF substance after administration to a patient in need thereof and consequently leading to improved means for optimizing dosage regimen of the active AF and/or AF peptide.

The present invention for the first time identifies AF's major metabolite as a cysteine disulfide of AF16 (AF-17). The rapid disulfide formation of AF16, being reversible, clearly protects AF16 from rapid peptidase degradation and is a protective function which enables AF16 to reach its target intact to a much higher degree, and/or which improves means for monitoring the fate of the active AF substance after administration to a patient in need thereof and consequently leads to an optimized dosage regimen of the active AF and/or AF peptide.

As revealed herein, the present inventors for the first time synthesize and study the in vitro pharmacokinetic properties of AF-17, proving that AF-17 can be administered directly to a patient in need thereof and that AF-17 is at least as effective as AF-16 for normalizing pathological fluid transport and/or inflammatory reactions, such as in the intestine, after challenge with the cholera toxin, as is shown e.g. in experiment 3. Given that AF-16 has prior been shown to be effective in a vast variety of different diseases and condition, selected from but not limited to normalizing pathological fluid transport and/or inflammatory reactions, treating and/or preventing TBI, tumors and/or tumor related complications, for treating cancer, compartment syndrome, glioblastoma, diabetes and diarrhea, for optimizing cellular uptake of a given drug, such as a small molecular drug, for neuroprotection, as well as for normalizing calveola, and AF-17 is the naturally occurring metabolite of AF-16, it can be assumed that the herein disclosed AF-17 is at least as effective as AF-16 for treating the same diseases and/or conditions as AF-16 is known to be effective for.

Thus, the present invention discloses a new and improved isolated recombinant or synthetic active peptide consisting of, comprising, derived from and/or based on the antisecretory factor (AF) protein (AF-17) and its use(s) in medicine. In particular, the present invention relates to the use of the herein described AF-17 for treating Traumatic Brain Injury (TBI).

What is more, as it is well known from extensive studies of the antisecretory protein (AF) over many years, the endogenous protein is post-transcriptionally processed into a plethora of smaller peptides, all with proven similar antisecretory effect, as long as the core active sequence of the protein (AF-6, shown in SEQ.ID.NO. 2) is intact. It thus stands to reason, that in the natural environment, the antisecretory protein (AF) will be degraded and/or post-transcriptionally processed into smaller peptides comprising AF-6, and that the metabolite of those smaller peptides will in analogy to the observed fate of AF-16, also be protected at least by a disulfide in the only cysteine of AF-6, i.e. in amino acid position 1 of AF-6, as shown in SEQ.ID.NO. 2.

The present invention thus further relates to an isolated recombinant and/or synthetically produced peptide, or a pharmaceutically active salt thereof, having equivalent functional activity, said peptide corresponding to a fragment of the antisecretory factor (AF) protein as shown in SEQ.ID.NO. 1 (AF) and/or a homologue thereof, having equivalent activity, wherein said peptide at least comprises an amino acid sequence as shown in SEQ.ID.NO. 2 (AF-6) and a cysteine disulfide in amino acid position no. 1 of SEQ.ID.NO. 2, said peptide having antisecretory activity and an improved in vitro half-life ($t_{1/2}$) compared to a peptide consisting of an identical fragment of the antisecretory factor (AF) protein shown in SEQ.ID.NO. 1 (AF) and/or a homologue thereof, wherein said peptide does not comprise a cysteine disulfide in amino acid position no. 1 of SEQ.ID.NO. 2.

In a presently preferred embodiment, the isolated recombinant and/or synthetically produced peptide of the present invention comprises an amino acid sequence as shown in SEQ.ID.NO. 3 (AF-16) and a cysteine disulfide in amino acid position no. 2 of SEQ.ID.NO. 3.

An isolated recombinant and/or synthetically produced peptide according to the present invention is 6-25 amino acids long, preferably 7-17, 6-16, 7-20, 7-17, 16-25, 16-20, 17-20, 17-25, such as 6, 7, 8, 9, 16 or 17 amino acids long. In certain embodiments, it is at least 6, 7, 16, or 17 amino acids long and/or at the most 7, 8, 9, 10, 11, 12, 13, 14, 15, 16, 17, 18, 19, 20, 21, 22, 23, 24, or 25 amino acids long.

An isolated recombinant and/or synthetically produced peptide according to the present invention typically comprises the amino acid sequence (VC(C)HSKTRSN-PENNVGL), as shown in SEQ.ID.NO. 7, or the amino acid sequence (C(C)HSKTR) as shown in SEQ.ID.NO. 8, or the amino acid sequence (VC(C)HSKTR) as shown in SEQ.ID.NO. 9.

An isolated recombinant and/or synthetically produced peptide according to the present invention typically consists of the amino acids (VC(C)HSKTRSNPENNVGL) as shown in SEQ.ID.NO. 7, or the amino acid sequence (C(C)HSKTR) as shown in SEQ.ID.NO. 8, or the amino acid sequence (VC(C)HSKTR) as shown in SEQ.ID.NO. 9.

An isolated recombinant and/or synthetically produced peptide according to the present invention typically has a t½ of at least 0.2 h, preferably of at least 0.25 h, 0.3 h, 0.4 h, 0.5 h, 1 h, or 1.5 h, 1.9 h, 2.0 h, 2.5 h, such as a t½ of at least 1.8 h.

The present invention further relates to an isolated recombinant and/or synthetically produced peptide according to the present invention for use in medicine, such as for use in treating and/or preventing diseases and conditions selected from the list consisting of pathological fluid transport, infections, inflammations, inflammatory reactions, TBI, TBI related conditions, tumors, tumor related complications, cancer, compartment syndrome, glioblastoma, diabetes, and diarrhea. The present invention further relates to an isolated recombinant and/or synthetically produced peptide according to the present invention for optimizing cellular uptake of an active substance, for neuroprotection and/or for normalizing calveola.

In one embodiment, a pharmaceutical and/or cosmetic composition is envisioned, comprising an isolated recombinant and/or synthetically produced peptide according to the present invention and a suitable pharmaceutical carrier.

A pharmaceutical and/or cosmetic composition according to the present invention is intended for use in treating and/or preventing diseases and conditions selected from the list consisting of pathological fluid transport, infections, inflammations, inflammatory reactions, TBI, TBI related conditions, tumors, tumor related complications, cancer, compartment syndrome, glioblastoma, diabetes, and diarrhea. The present invention further relates to a pharmaceutical and/or cosmetic composition according to the present invention for optimizing cellular uptake of an active substance, for neuroprotection and/or for normalizing calveola.

Also related to is a method of normalizing pathological fluid transport and/or inflammatory reaction in patient in need thereof, and/or a method for optimizing cellular uptake of an active substance, for neuroprotection and/or for normalizing calveola and/or for treating and/or preventing diseases and conditions selected from the list consisting of pathological fluid transport, infections, inflammations, inflammatory reactions, TBI, TBI related conditions, tumors, tumor related complications, cancer, compartment syndrome, glioblastoma, diabetes, and diarrhea, comprising administering to an animal or a human being in need thereof an effective amount of an isolated recombinant and/or synthetically produced peptide according to the present invention or a pharmaceutical composition comprising said peptide.

The present invention in addition relates to an antibody against a peptide having essentially the amino acid sequence shown in SEQ.ID.NO. 7, 8 or 9, as well as to its use in detecting said protein or homologues or fragments thereof in organisms, such as animals, including mammalians and humans.

Also provided herein is the use of a nucleic acid coding for a peptide having essentially the amino acid sequence shown in any of SEQ. ID. NO. 1-9, for producing a corresponding peptide, wherein said peptide comprises at least one cysteine disulfide in at least amino acid (aa) position no. 36 of SEQ.ID.NO. 1, in aa position no. 1 of SEQ.ID.NO. 2, in aa position no. 2 of SEQ.ID.NO. 3, and/or in aa position no. 2 of SEQ.ID.NO. 4.

FIGURE LEGENDS

FIG. 1 Oxidation of cysteine. A: Sulfenic acid, B: Sulfinic acid, C: Sulfonic acid FIG. 2 N-ethyl maleimide analog of AF16 (AF16-NEM)

FIG. 3 Human plasma and buffer stability of AF16 (A) and AF16-NEM (B)

Figure 4:
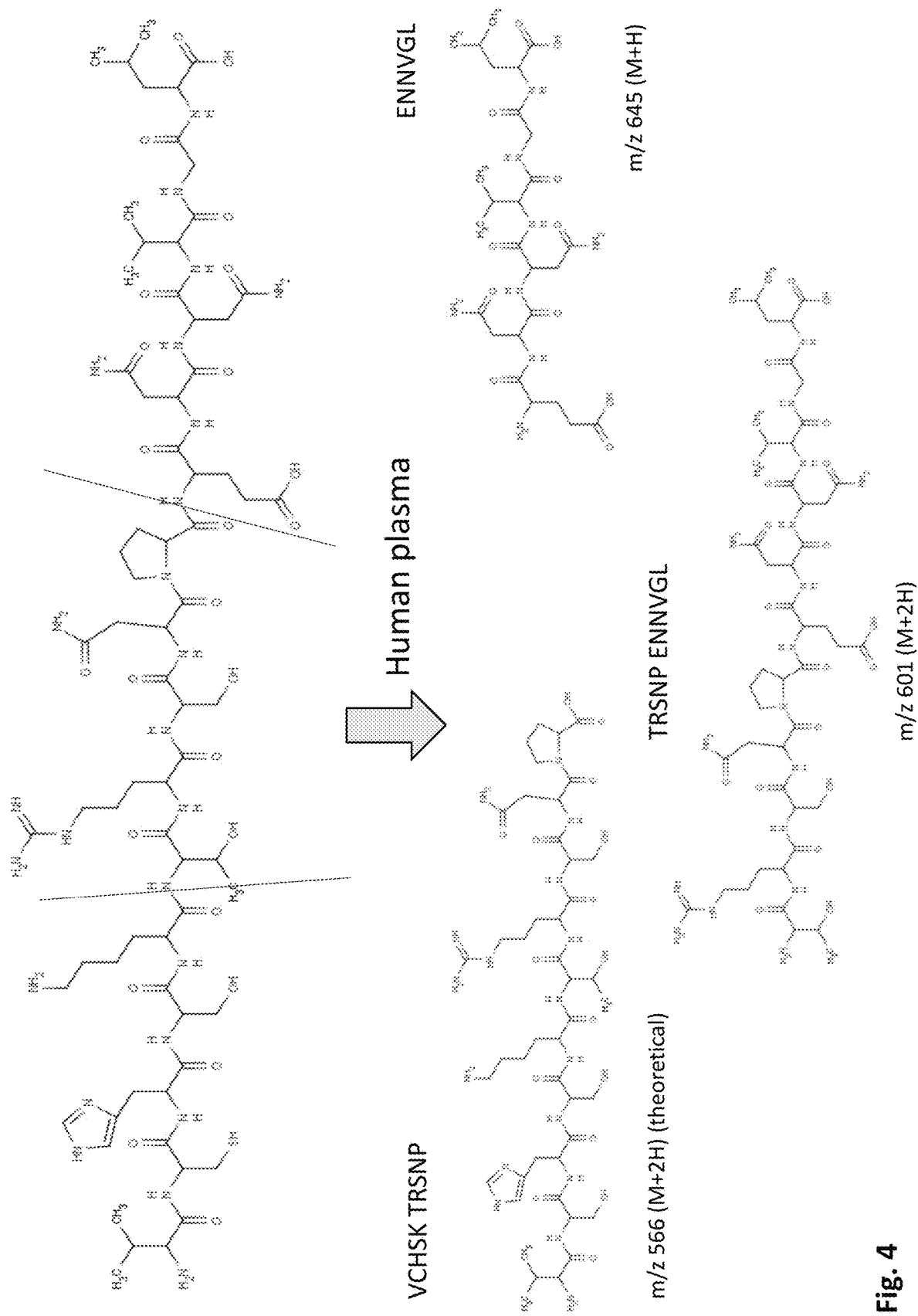

FIG. 4 LC-MS detected degradation products of AF16 in human plasma

Figure 5:
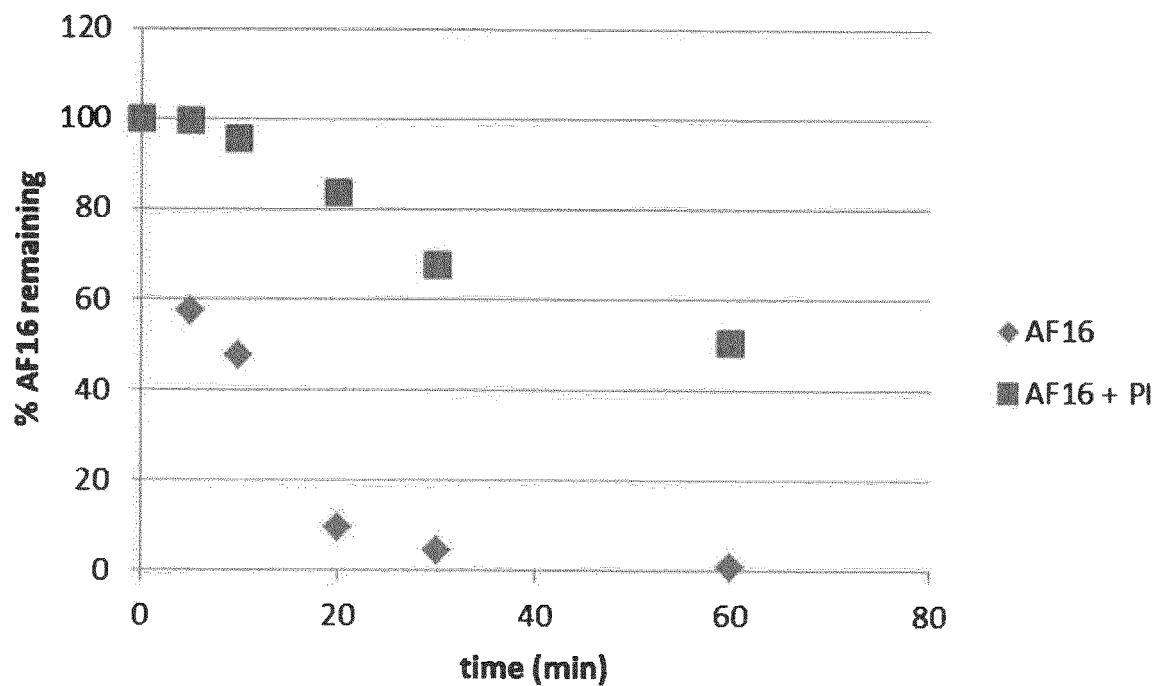
Figure 6:
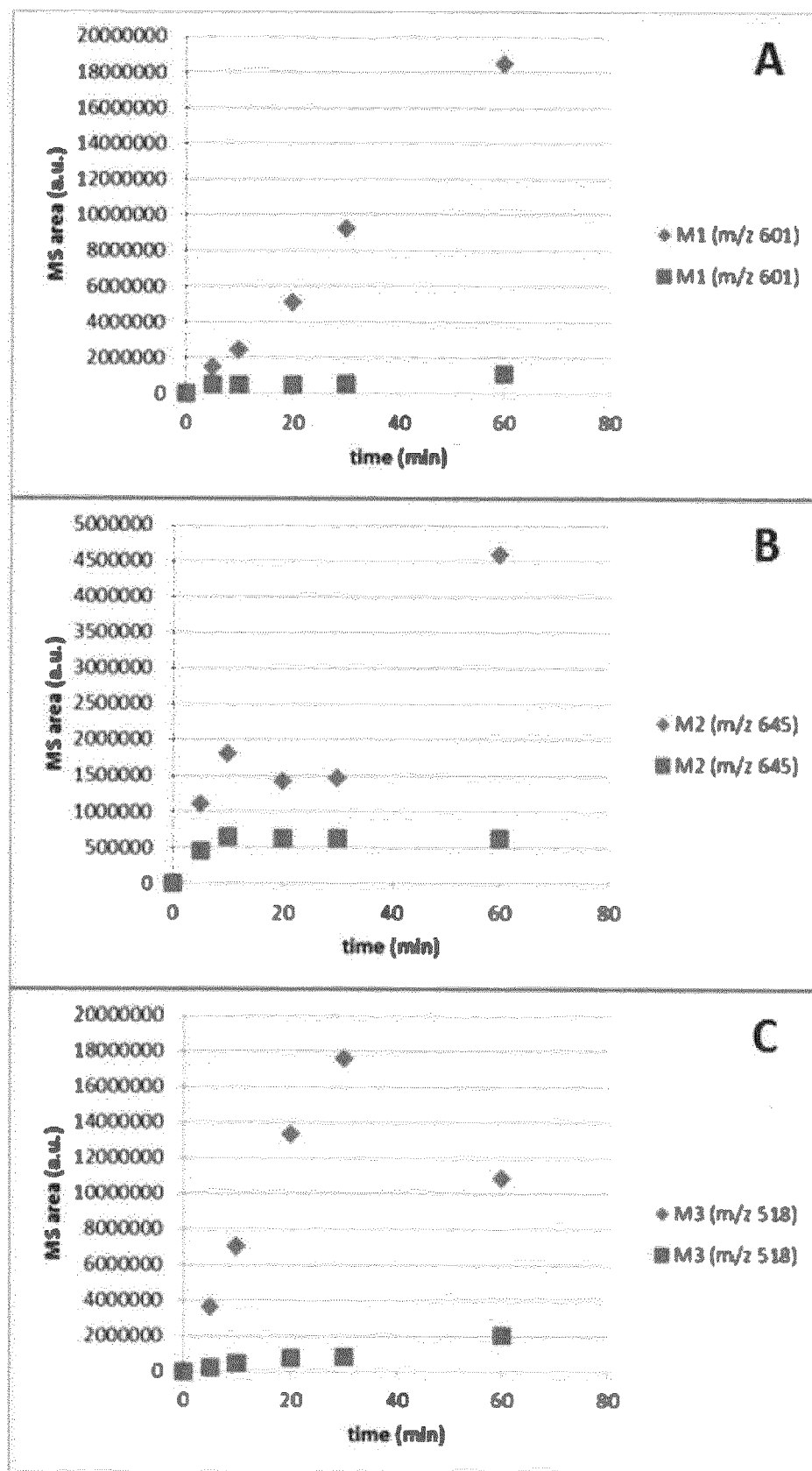
Figure 9:
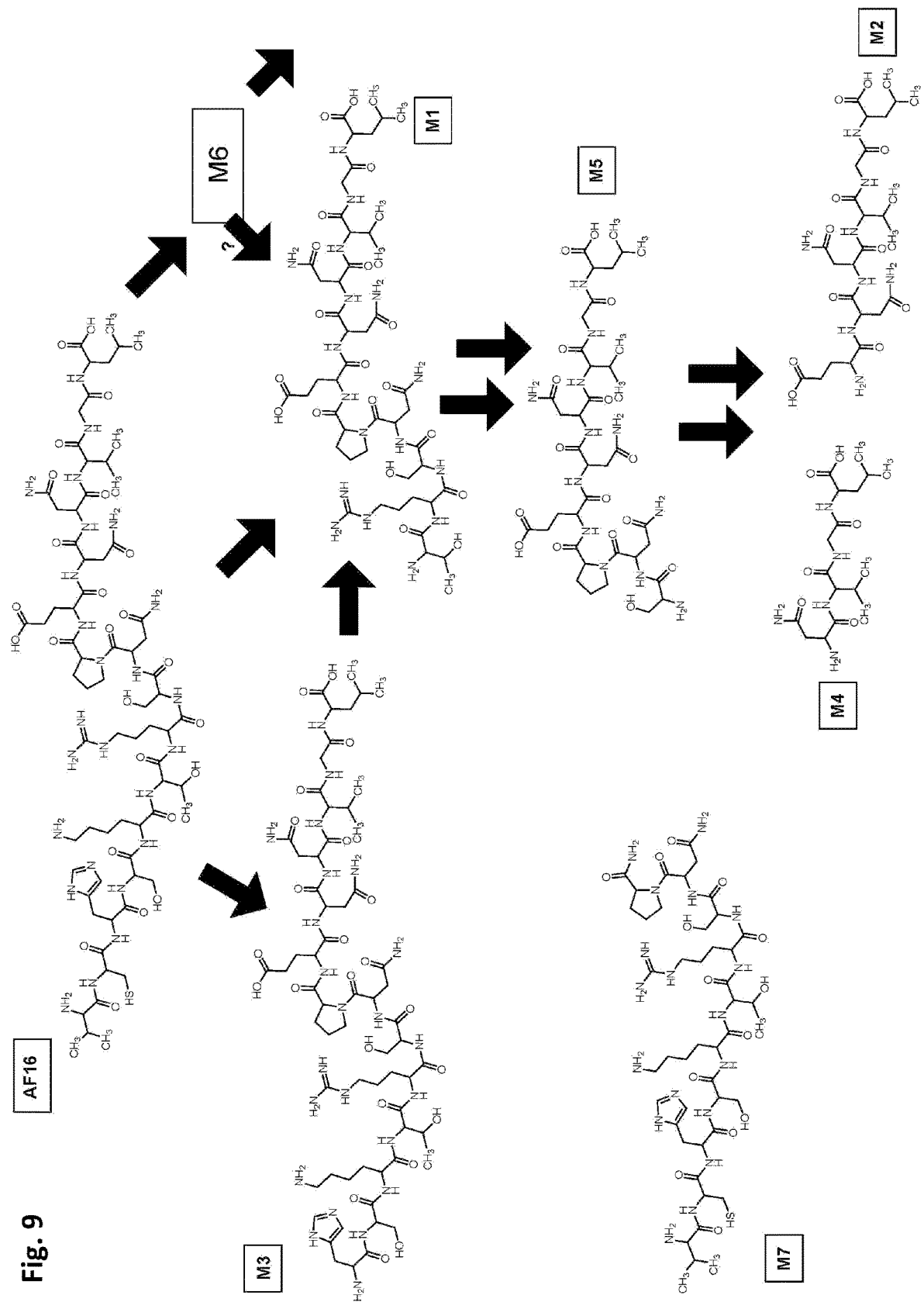
Figure 10:
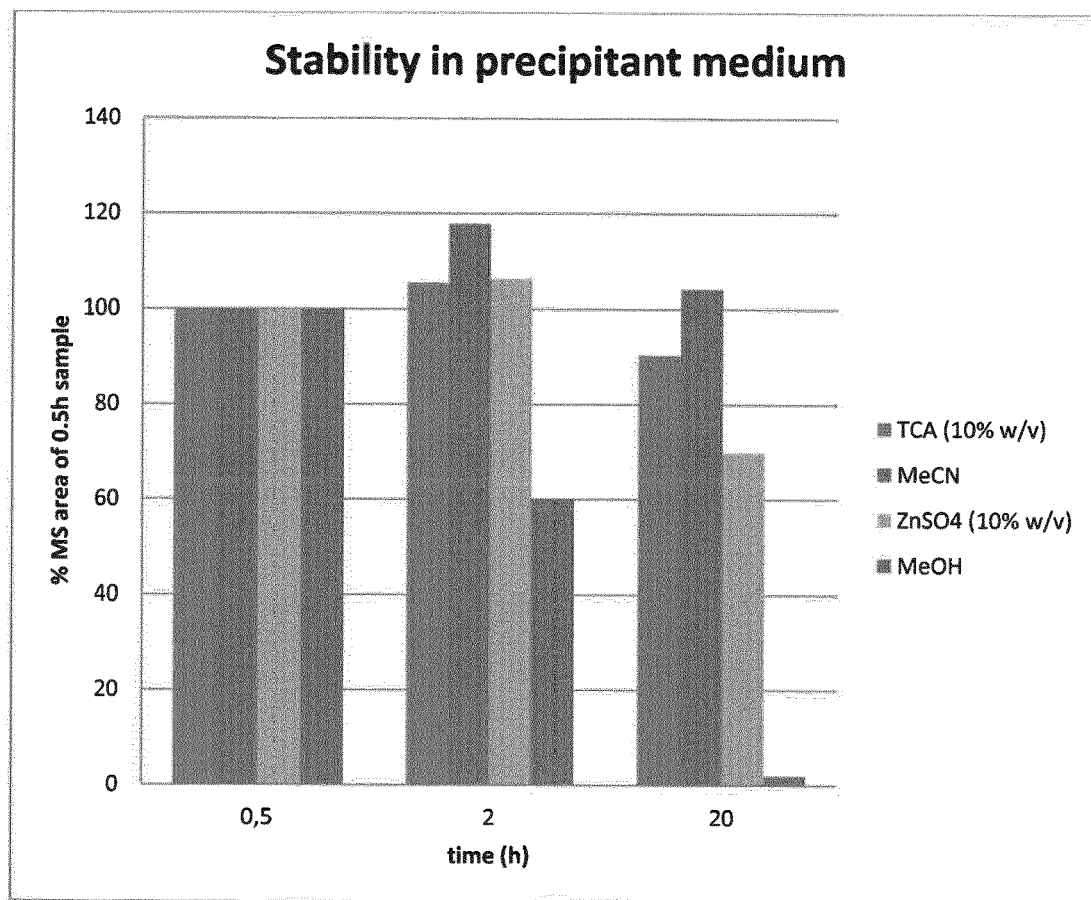

FIG. 5 AF16 degradation in the presence of Caco-2 cells. +PI indicates protease inhibitor cocktail FIG. 6 Metabolite formation kinetics of AF16 degradation in the presence of Caco-2 cells. Blue diamond AF16. Red square AF16+inhibitor cocktail FIG. 7 Metabolite formation kinetics of AF16 degradation in the presence of Caco-2 cells. Blue diamond AF16. Red square AF16+inhibitor cocktail FIG. 8 Metabolite formation kinetics of AF16 degradation in the presence of Caco-2 cells. Blue diamond AF16. Red square AF16+inhibitor cocktail FIG. 9 Degradation of AF16 in the presence of Caco-2 cells. Suggested pathways of determined structures FIG. 10 Relative stability of AF16 with different precipitation methods over 20 h at 10° C. FIG. 10 shows the results of repeated injection of the same sample three times over 20 h. It is clear that TCA and MeCN shows good apparent stability over time. A slight disappearance is noted with ZnSO4 at 20 h. A significant loss over time is shown with MeOH. It is likely that AF16 is stable with MeOH but the loss stem from peptide precipitation since it is known that peptides may have limited solubility in alcoholic mixtures.

Figure 11:
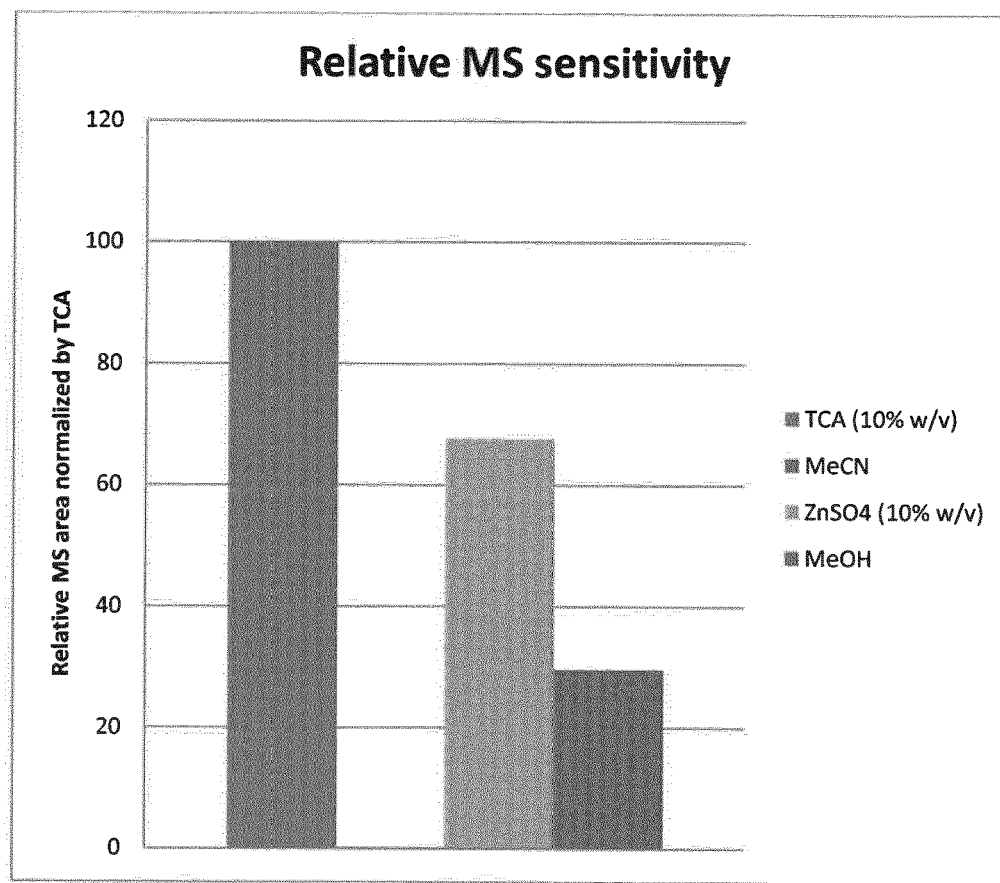

FIG. 11 Relative stability of AF16 with different precipitation methods over 20 h at 10° C. FIG. 11 shows a diagram of the data acquired above in comparison to each other in terms of MS-intensity (ion counts). TCA precipitation showed the strongest signal and was set as the reference. It is clear that the nonorganic methods fall behind, most likely due to co-eluting suppressing ions. The two methods with best stability (TCA and MeCN) show over 500-fold difference in sensitivity, thus for the continued studies, TCA was chosen to be used throughout the study.

FIG. 12 Relative stability of AF16 with different precipitation methods over 20 h at 10° C.

Figure 13A:
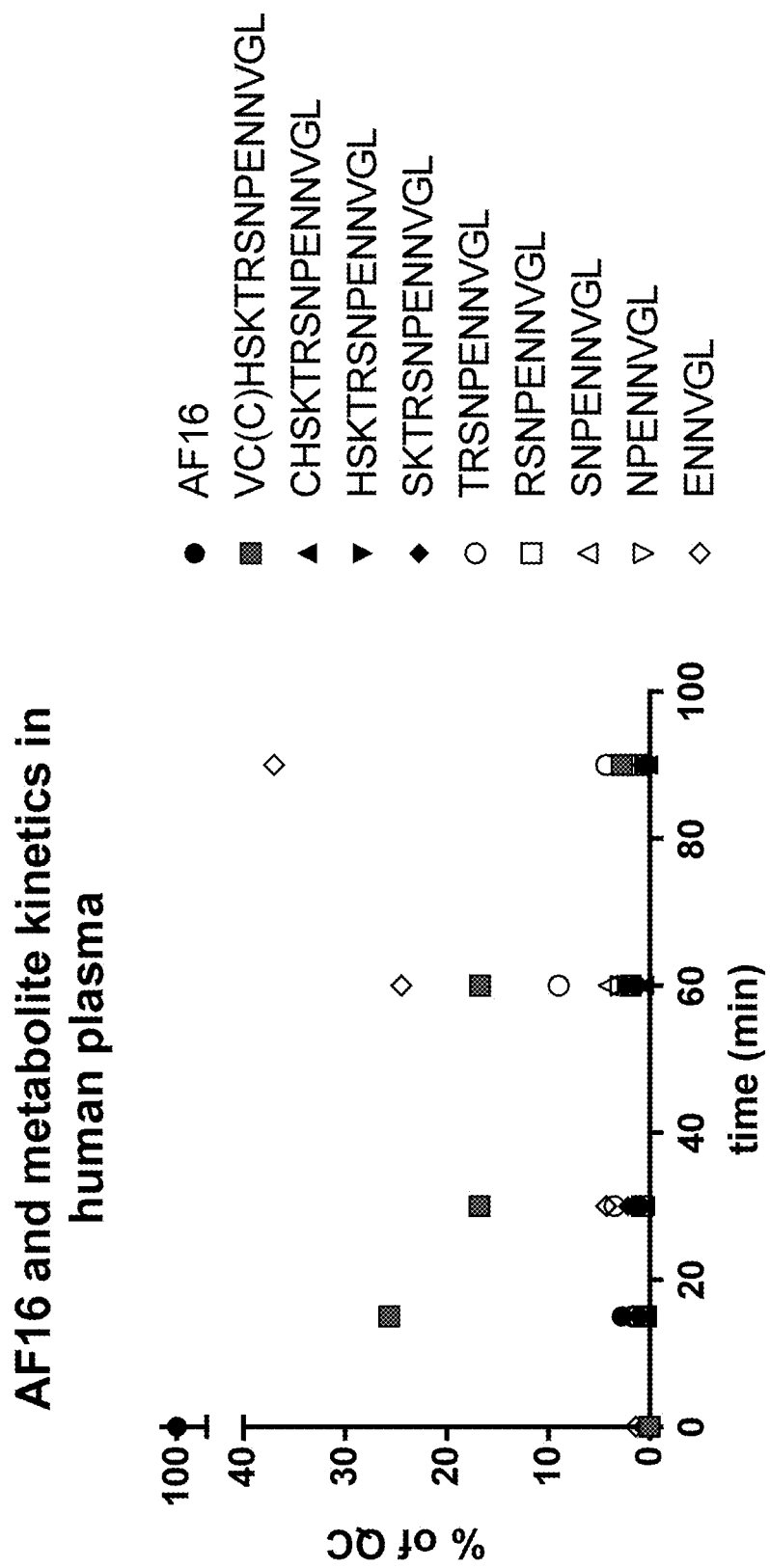
Figure 13B:
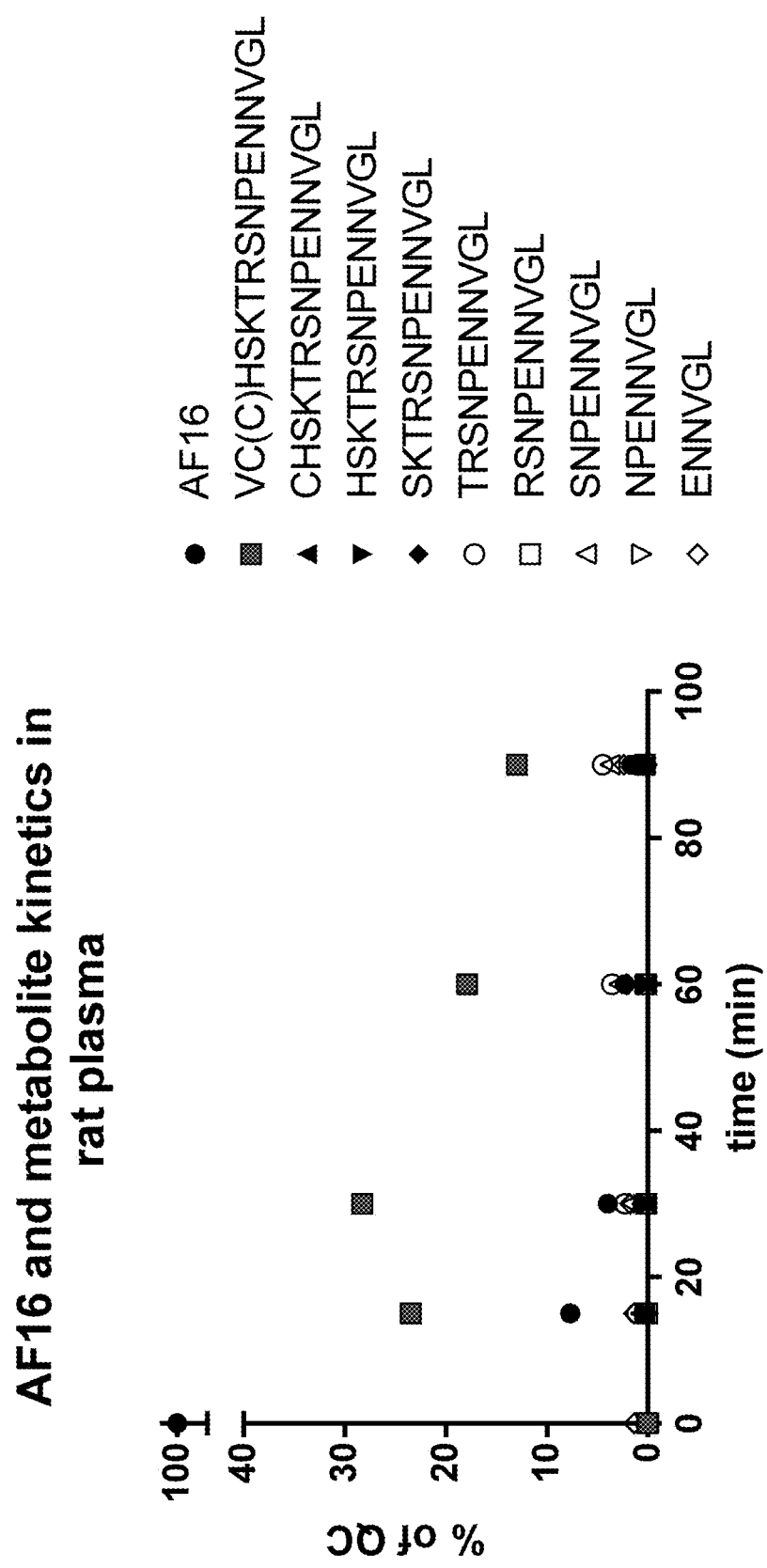
Figure 14:
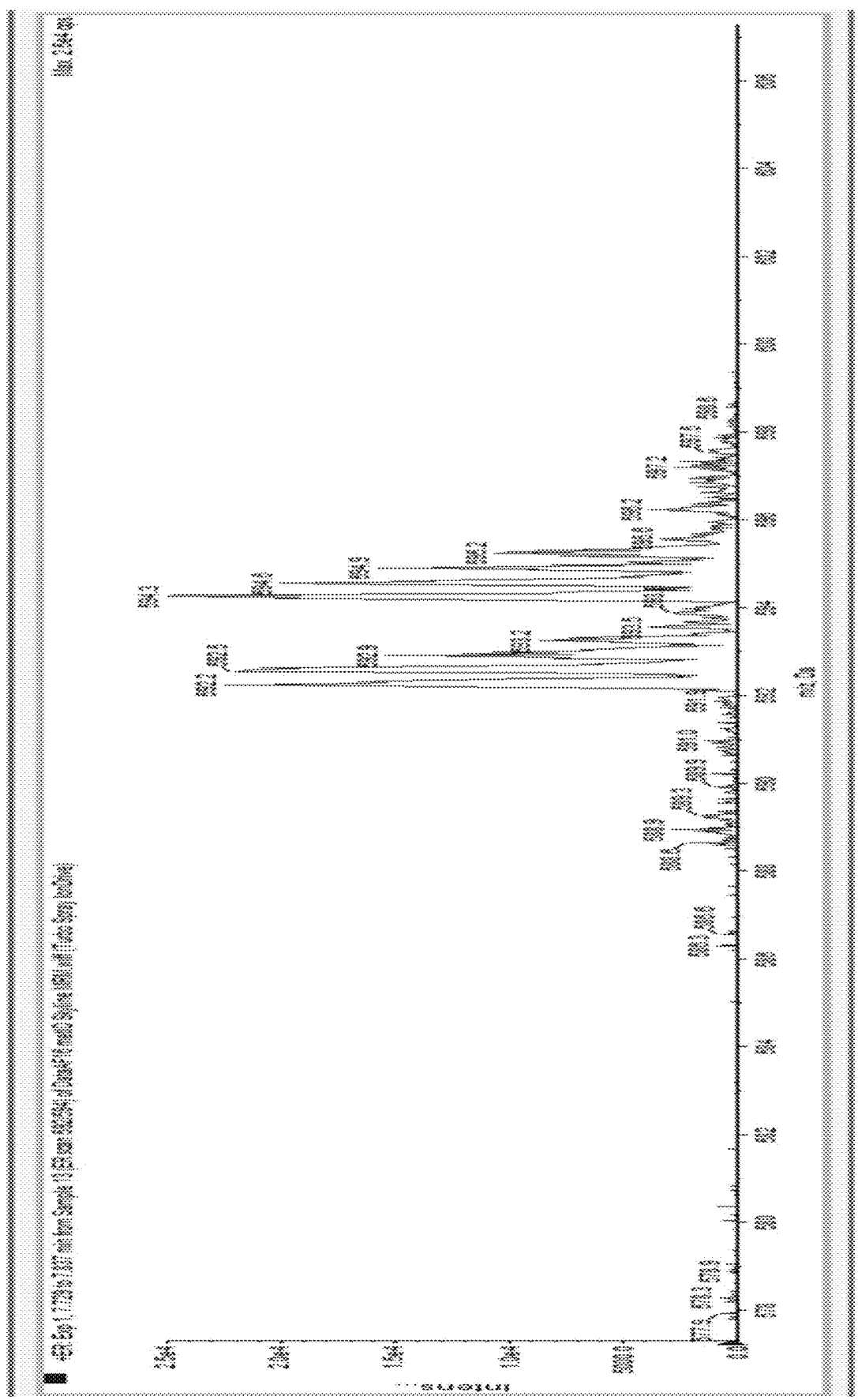
Figure 15:
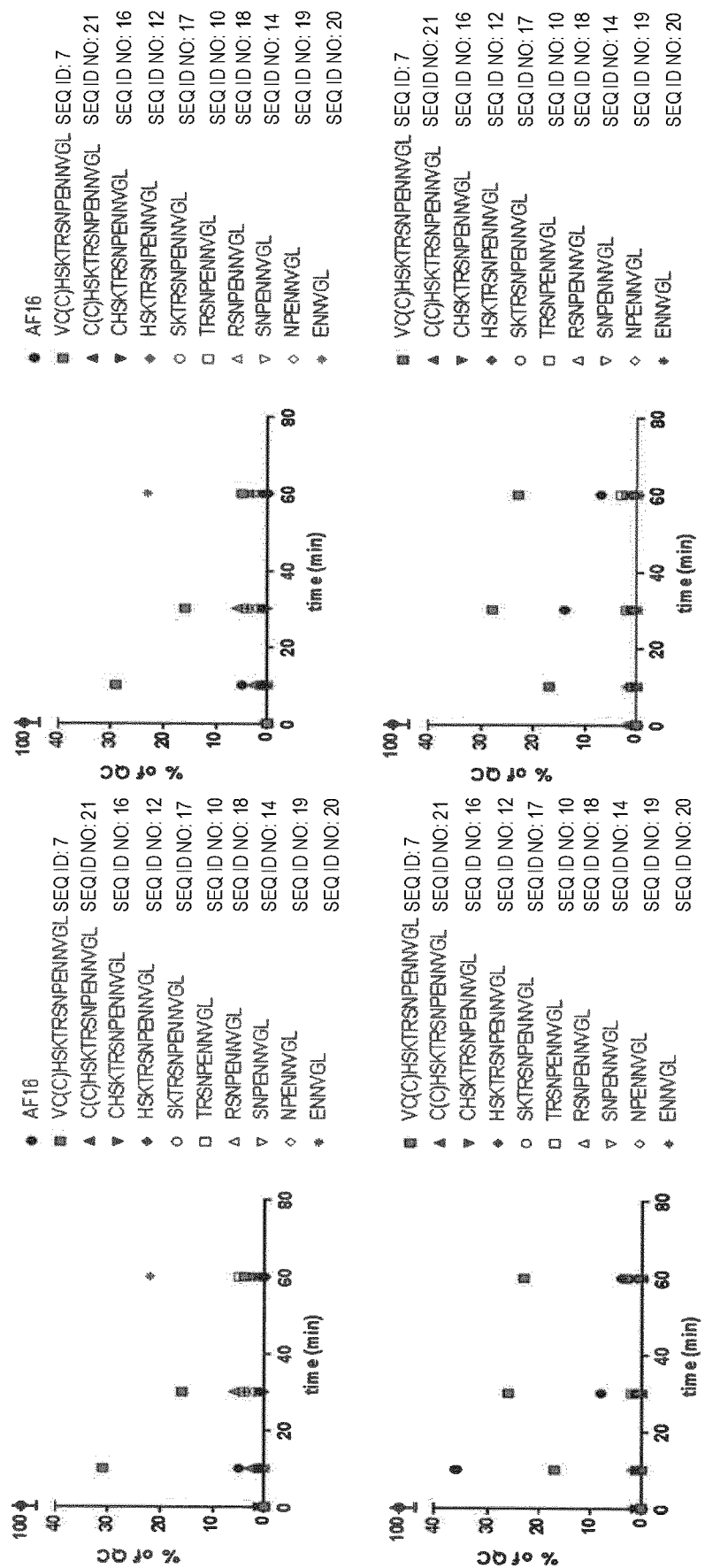
Figure 16:
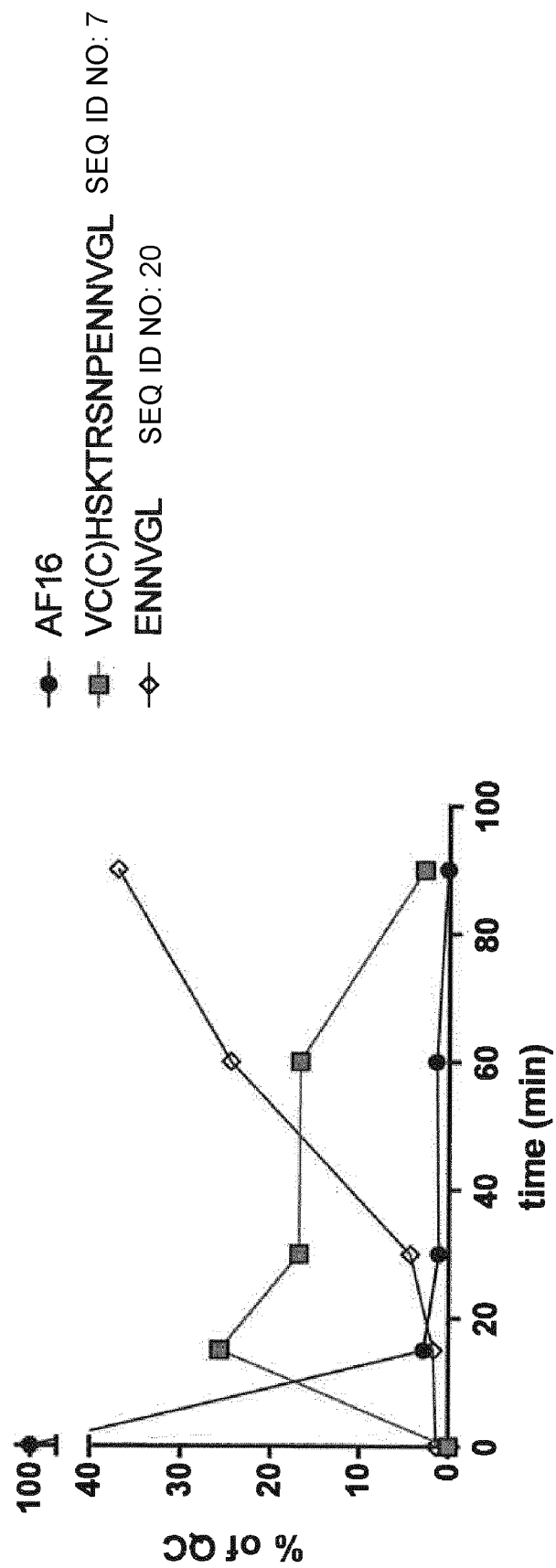
Figure 17:
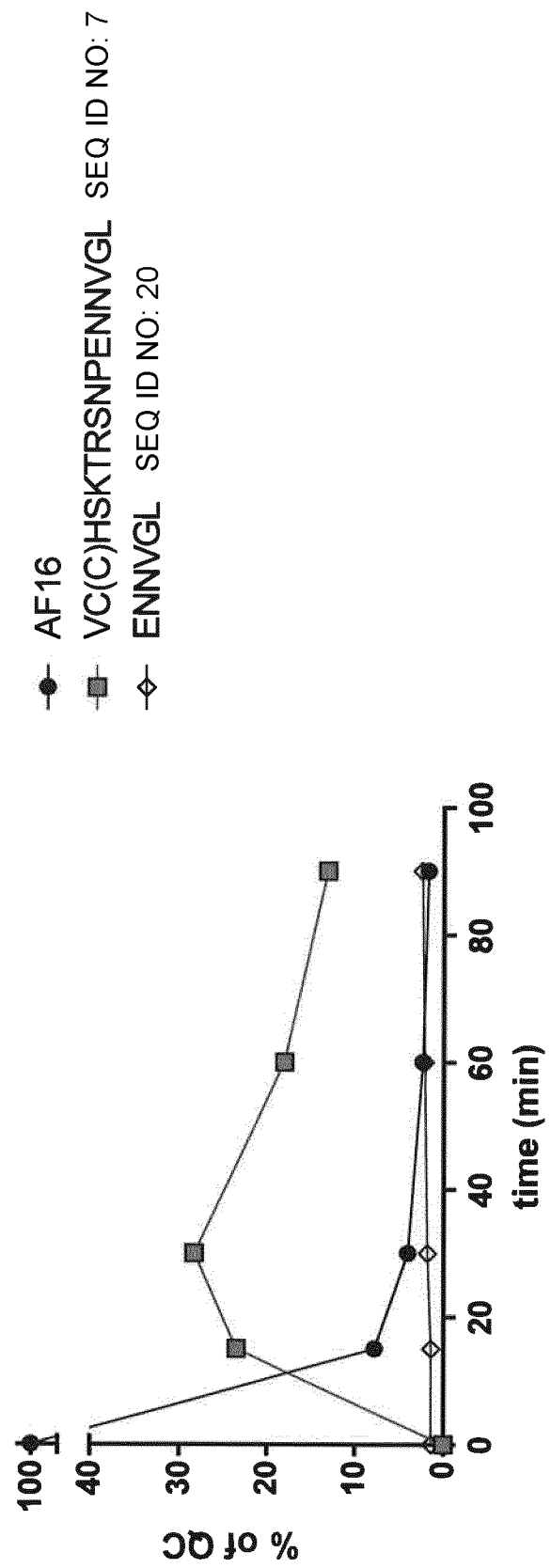

FIG. 13 Kinetics of AF16 and the identified metabolites in human (top) and rat (bottom) plasma FIG. 14 Enhanced resolution scan of the 592.3/594.4 metabolite FIG. 15 Kinetics of AF16 and the identified metabolites using ZnSO4 as plasma precipitant and +/−DTT. A: human+DTT, B: human−DTT, C: rat+DTT and D: rat−DTT. AF16 is shown in full circle FIG. 16 Relative formation of major identified products in human plasma FIG. 17 Relative formation of major identified products in rat plasma

DEFINITIONS AND ABBREVIATIONS

Abbreviations

IFP: interstitial fluid pressure;
PBS: phosphate buffered saline;
AF: antisecretory factor, Full-length AF protein (as shown in SEQ.ID.NO. 1)
AF-6: a hexa peptide CHSKTR (as shown in SEQ.ID.NO. 2);
AF-7: a peptide composed of the amino acids C(C)HSKTR (as shown in SEQ.ID.NO. 8);
AF-16: a peptide composed of the amino acids VCHSKTRSNPENNVGL (as shown in SEQ.ID.NO. 3);
AF-17: a peptide composed of the amino acids VC(C)HSKTRSNPENNVGL (as shown in SEQ.ID.NO. 7);
AF-8: a septa peptide VCHSKTR (as shown in SEQ.ID.NO. 4);
AF-9: a peptide composed of the amino acids VC(C)HSKTR (as shown in SEQ.ID.NO. 9);
Octa peptide IVCHSKTR (as shown in SEQ.ID.NO. 5);
Penta peptide HSKTR (as shown in SEQ.ID.NO. 6);
SPC: Specially Processed Cereals;
RTT: Method for measuring a standardized secretion response in rat small intestine, as published in SE 9000028-2 (publication number 466331) for measuring content of AF (ASP);
AF: Antisecretory Factor;
ELISA: Enzyme-linked immunosorbent assay;
PBS: phosphate buffered saline;
AP: alkaline phosphatase;
BSA: bovine serum albumin;
mAb: monoclonal antibody;
LC-MS/MS: nanoflow liquid chromatography-tandem mass spectrometry;
PAGE: polyacrylamide gel electrophoresis.
HSV1: herpes simplex virus-1
TBI: Traumatic Brain Injury

Definitions

Proteins are biological macromolecules constituted by amino acid residues linked together by peptide bonds. Proteins, as linear polymers of amino acids, are also called polypeptides. Typically, proteins have 50-800 amino acid residues and hence have molecular weights in the range of from about 6,000 to about several hundred thousand Dalton or more. Small proteins are called peptides, polypeptides, or oligopeptides. The terms "protein", "polypeptide", "oligopeptide" and "peptide" may be used interchangeably in the present context. Peptides can have very few amino acid residues, such as between 2-50 amino acid residues (aa).

The term "antisecretory" refers in the present context to inhibiting or decreasing secretion and/or fluid transfer. In the present context, the terms an "Antisecretory factor protein", "antisecretory factor (AF) protein", "AF-protein", AF, or a homologue, derivative or fragment thereof, may be used interchangeably with the term "antisecretory factors" or "antisecretory factor proteins" as defined in WO 97/08202, and refer to an antisecretory factor (AF) protein or a peptide or a homologue, derivative and/or fragment thereof having antisecretory and/or equivalent functional and/or analogue activity, or to a modification thereof not altering the function of the polypeptide. Hence, it is to be understood that an "antisecretory factor", "antisecretory factor protein", "antisecretory peptide", "antisecretory fragment", or an "antisecretory factor (AF) protein" in the present context, also can refer to a derivative, homologue or fragment thereof. These terms may all be used interchangeably in the context of the present invention. Furthermore, in the present context, the term "antisecretory factor" may be abbreviated "AF". Antisecretory factor (AF) protein in the present context also refers to a protein with antisecretory properties as previously defined in WO97/08202 and WO 00/38535. Antisecretory factors have also been disclosed e.g. in WO 05/030246.

SPC© is a medical food comprising specially processed cereals (SPC).

A "medical food", in the present context, refers to a food, a feed or food supplement, or a food for special dietary use, which has been prepared with an antisecretory factor (AF) protein, or alternatively, has the capability to induce synthesis and/or activation of endogenous AF. Said food may be any suitable food, in fluid or solid form, such as a liquid or a powder, or any other suitable foodstuff. Examples of such matter may be found in WO 0038535 or WO 91/09536.

Salovum© Also intended by the term antisecretory factor are native antisecretory factors (NASP) which can be provided in egg yolk with a high content of antisecretory factors (NASP), as e.g. disclosed in SE 900028-2 and WO 00/38535, and as further described below.

DETAILED DESCRIPTION OF THE INVENTION

The present invention for the first time identifies AF's major metabolite as a cysteine disulfide of AF16 (AF-17). The rapid disulfide formation of AF16, being reversible, clearly protects AF16 from rapid peptidase degradation and is a protective function which enables AF16 to reach its target intact to a much higher degree, and improves means for monitoring the fate of the active AF substance after administration to a patient in need thereof and consequently leads to an optimized dosage regimen of the active AF substance, full-length AF, a fragment of AF and/or AF peptide. As is for the first time documented herein, disclosed is a new synthetically produced or isolated recombinant AF-peptide (AF-17) with improved in vitro half-life ($t_{1/2}$), enabling improved means for monitoring the fate of the active AF substance after administration to a patient in need thereof and consequently leading to improved means for optimizing dosage regimen of the active AF and/or AF peptide.

In one embodiment, the present invention relates to an isolated recombinant and/or synthetically produced peptide hereinafter called AF-17 (as shown in SEQ.ID.NO. 7), or a pharmaceutically active salt thereof, having equivalent functional activity, which comprises an amino acid sequence as shown in SEQ.ID.NO. 3 (AF-16) and a cysteine disulfide in amino acid position no. 2 of SEQ.ID.NO. 3, said peptide having antisecretory activity.

In another embodiment, the present invention relates to an isolated recombinant and/or synthetically produced peptide, hereinafter referred to as AF-7 (as shown in SEQ.ID.NO. 8), or a pharmaceutically active salt thereof, having equivalent functional activity, which comprises an amino acid sequence as shown in SEQ.ID.NO. 2 (AF-6) and a cysteine disulfide in amino acid position no. 1 of SEQ.ID.NO. 3, said peptide having antisecretory activity.

In yet another embodiment, the present invention relates to an isolated recombinant and/or synthetically produced peptide, hereinafter referred to as AF-9 (as shown in SEQ.ID.NO. 9), or a pharmaceutically active salt thereof, having equivalent functional activity, which comprises an amino acid sequence as shown in SEQ.ID.NO. 4 (AF-8) and a cysteine disulfide in amino acid position no. 2 of SEQ.ID.NO. 4, said peptide having antisecretory activity.

As revealed herein, the present inventors for the first time disclose a peptide according to the present invention which is at least as effective as AF-16 for normalizing pathological fluid transport and/or inflammatory reactions, such as in the intestine, after challenge with the cholera toxin, as is shown e.g. in experiment 3. A peptide according to the present invention is effective in a vast variety of different diseases and condition, selected from but not limited to normalizing pathological fluid transport and/or inflammatory reactions, treating and/or preventing TBI, tumors and/or tumor related complications, for treating cancer, compartment syndrome, glioblastoma, diabetes and diarrhea, for optimizing cellular uptake of a given drug, for neuroprotection, as well as for normalizing calveola.

Thus, the present invention discloses a new and improved isolated recombinant or synthetic active peptide consisting of, comprising, derived from and/or based on the antisecretory factor (AF) protein (AF-17) and its use(s) in medicine. In particular, the present invention relates to the use of one or a combination of the herein described AF-17, AF-7, and/or AF-9 for treating and/or preventing diseases and conditions selected from the list consisting of pathological fluid transport, infections, inflammations, inflammatory reactions, TBI, TBI related conditions, tumors, tumor related complications, cancer, compartment syndrome, glioblastoma, diabetes, and diarrhea, or for optimizing cellular uptake of an active substance, for neuroprotection and/or for normalizing calveola.

The present invention discloses a new and improved isolated recombinant or synthetic active peptide consisting of, comprising, derived from and/or based on the antisecretory factor (AF) protein (AF-17) and in particular a new peptide called Antisecretory Factor (AF) 17. The peptide is e.g. used for normalizing pathological fluid transport and/or inflammatory reactions in animals including humans. AF-17 can further be used for immunodetection, as feed additive for growing animals and as antidiarrheal and drug against diseases involving edema, dehydration and/or inflammation.

The Antisecretory Factor

The antisecretory factor is a class of proteins that occurs naturally in the body. The human antisecretory factor AF protein is a 41 kDa protein, comprising 382-288 amino acids when isolated from the pituitary gland. The active site according to the present invention can be localized to the protein in a region close to the N-terminal of the protein, in particular localized to amino acids 1-163 of SEQ ID NO 1, more specifically to amino acid positions 35-50 on the antisecretory factor (AF) protein sequence. The biological effect of AF is exerted by any peptide or polypeptide comprising at least 6 amino acids, as shown in SEQ.ID.NO. 2 (AF-6), of said consensus sequence, or comprising a modification thereof not altering the biological function of the polypeptide and/or peptide.

The present inventors have shown that the antisecretory factor is to some extent homologous with the protein S5a, and Rpn10, which constitutes a subunit of a constituent prevailing in all cells, the 26 S proteasome, more specifically in the 19 S/PA 700 cap. In the present invention, antisecretory factor (AF) proteins are defined as a class of homologue proteins having the same functional properties. Antisecretory factor is also highly similar to angiocidin, another protein isoform known to bind to thrombospondin-1 and associated with cancer progression.

Homologues, derivatives and fragments of antisecretory factor (AF) proteins and/or peptides according to the present invention all have analogous biological activity. Homologues, derivatives and fragments, in the present context, comprise at least 6 amino acids (as shown in SEQ.ID.NO. 2) corresponding to those of a naturally occurring antisecretory factor (AF) protein, which may be further modified by changing one or more amino acids in order to optimize the antisecretory factor's biological activity, without altering the essential biological function of the polypeptide and/or peptide.

By a derivative is in the present context intended a protein having equivalent activity and/or a functional equivalent activity to an antisecretory factor as defined herein, being derived from another substance either directly or by modification or partial substitution, wherein one or more amino acids have been substituted by another amino acid, which amino acid can be a modified or an unnatural amino acid. For example, the antisecretory factor derivatives according to the invention may comprise an N terminal and/or a C terminal protecting group. One example of an N terminal protecting group includes acetyl. One example of a C terminal protecting group includes amide.

Furthermore, any amino acid sequence being at least 70% identical, such as being at least 72%, 75%, 77%, 80%, 82%, 85%, 87%, 90%, 91%, 92%, 93%, 94%, 95%, 96%, 97%, 98%, or 99% identical with the amino acid sequence of an antisecretory factor (AF) protein, peptide, homologue, derivative and/or fragment according to the invention, is also considered to be inside the scope of the present invention.

By proteins, homologues, derivatives, peptides and/or fragment thereof having an amino acid sequence at least, for example 95% identical to a reference amino acid sequence, is intended that the amino acid sequence of e.g. the peptide is identical to the reference sequence, except that the amino acid sequence may include up to 5 point mutations per each 100 amino acids of the reference amino acid sequence. In other words, to obtain a polypeptide having an amino acid sequence at least 95% identical to a reference amino acid sequence, up to 5% of the amino acids in the reference sequence may be deleted or substituted with another amino acid, or a number of amino acids up to 5% of the total amino acids in the reference sequence may be inserted into the reference sequence. These mutations of the reference sequence may occur at the amino or carboxy terminal positions of the reference amino acid sequence or anywhere between those terminal positions, interspersed either individually among amino acids in the reference sequence or in one or more contiguous groups within the reference sequence.

In the present invention, a local algorithm program is best suited to determine identity. Local algorithm programs, (such as Smith Waterman) compare a subsequence in one sequence with a subsequence in a second sequence, and find the combination of sub-sequences and the alignment of those sub-sequences, which yields the highest overall similarity score. Internal gaps, if allowed, are penalized. Local algorithms work well for comparing two multi domain proteins, which have a single domain, or just a binding site in common.

Methods to determine identity and similarity are codified in publicly available programs. Preferred computer program methods to determine identity and similarity between two sequences include, but are not limited to, the GCG program package (Devereux, J et al (1994)) BLASTP, BLASTN, and FASTA (Altschul, S. F. et al (1990)). The BLASTX program is publicly available from NCBI and other sources (BLAST Manual, Altschul, S. F. et al, Altschul, S. F. et al (1990)). Each sequence analysis program has a default scoring matrix and default gap penalties. In general, a molecular biologist would be expected to use the default settings established by the software program used.

The antisecretory factor (AF) proteins or a peptide or a homologue, derivative and/or fragment thereof having equivalent activity as defined herein, can comprise 6 amino acids or more, such as 6-16 amino acids, such as 6, 7, 8, 9, 10, 11, 12, 13, 14, 15, 16, 17, 18, 19 or 20 amino acids or more. In other preferred embodiments, the antisecretory factor consists of 7, 9 or 17 amino acids. In certain embodiments, the antisecretory factor (AF) protein, a homologue, derivative, peptide and/or fragment thereof, according to the present invention, consists of 6, 7, 8, 9, 15, 16 or 17 amino acids.

In a presently preferred embodiment, an isolated recombinant and/or synthetic peptide AF-17 (as shown in SEQ.ID.NO. 7), or a pharmaceutically active salt thereof, having equivalent functional activity, comprises an amino acid sequence as shown in SEQ.ID.NO. 3 (AF-16) and a cysteine disulfide in amino acid position no. 2 of SEQ.ID.NO. 3, said peptide having antisecretory activity.

In another preferred embodiment, an isolated recombinant and/or synthetic peptide, or a pharmaceutically active salt thereof, having equivalent functional activity, at least comprises an amino acid sequence as shown in SEQ.ID.NO. 2 (AF-6) and a cysteine disulfide in amino acid position no. 1 of SEQ.ID.NO. 2, said peptide having antisecretory activity.

In yet another preferred embodiment, an isolated recombinant and/or synthetic peptide, or a pharmaceutically active salt thereof, having equivalent functional activity, at least comprises an amino acid sequence as shown in SEQ.ID.NO. 4 (AF-8) and a cysteine disulfide in amino acid position no. 2 of SEQ.ID.NO. 4, said peptide having antisecretory activity.

The antisecretory factor (AF) protein, a homologue, derivative, peptide and/or fragment thereof, according to the present invention, can be produced in vivo or in vitro, e.g. recombinantly, synthetically and/or chemically synthesized, and/or isolated from a naturally occurring source of antisecretory factors, such as from pig pituitary glands or bird's eggs. After production, the antisecretory factor (AF) protein, homologue, derivative, peptide and/or fragment thereof, according to the present invention, may be further processed, such as by chemical or enzymatic cleavage to smaller antisecretory active fragments and/or by modification of amino acids and/or by addition of a cysteine in amino acid position no. 1 of SEQ.ID.NO. 2, alternatively in amino acid position no. 2 of SEQ.ID.NO. 3, via a disulfide link in the cysteine in the peptide.

It is presently not possible to obtain antisecretory factor (AF)-protein in pure form by purification. It is however possible to produce a biologically active antisecretory factor protein recombinantly or synthetically, as previously disclosed in WO 97/08202 and WO 05/030246. WO 97/08202 also discloses the production of biologically active fragments of this protein of 7-80 amino acids.

In the present context, the antisecretory factor (AF) protein, a homologue, derivative, peptide and/or fragment thereof, according to the present invention is either a natural metabolite of antisecretory factor (AF) protein produced in a mammal (excluding humans), or recombinantly produced and optionally chemically modified, or a synthetically produced peptide.

The antisecretory factor (AF) protein, a homologue, derivative, peptide and/or fragment thereof, according to the present invention, may further comprise an N terminal and/or a C terminal protecting group. One example of an N terminal protecting group includes acetyl. One example of a C terminal protecting group includes amide.

In a preferred embodiment of the present invention the antisecretory factor (AF) protein, a homologue, derivative, peptide and/or fragment thereof, according to the present invention is selected among SEQ ID NO 7-9, i.e. VC(C) HSKTRSNPENNVGL (SEQ ID NO 7, in this context also called AF-17), C(C)HSKTR (SEQ ID NO 8, in this context also called AF-7), VC(C)HSKTR (SEQ ID NO 9 in this context also called AF-9), using the common one letter abbreviations for amino acids. As specified in the accompanying sequence listing, some of the amino acids in the above-specified sequences may be replaced by other amino acids.

Also intended by the present invention is the combination of two or more of any of the peptides according to SEQ ID NO 7-9.

In yet another embodiment, the invention relates to the use of a pharmaceutical composition as disclosed herein, which comprises two or more the antisecretory factor (AF) protein, a homologue, derivative, peptide and/or fragment thereof, according to the present invention.

Disulfide

In the present context, a disulfide refers to a functional group with the general structure R—S—S—R. The linkage is also called an SS-bond or a disulfide bridge and is usually derived by the coupling of two thiol groups. In formal terms, the connection is a persulfide, in analogy to its congener, peroxide (R—O—O—R).

Cysteine (abbreviated as Cys or C) is a semi-essential proteinogenic amino acid with the formula HO2CCH(NH2)CH2SH>. It is encoded by the codons UGU and UGC. The thiol side chain in Cys often participates in enzymatic reactions, as a nucleophile. The thiol is susceptible to oxidization to give the disulfide derivative cysteine, which serves an important structural role in many proteins.

Cysteine residues are among the most chemically involved amino acids, participating typically in redox chemical reactions but also as a nucleophile against reactive electrophiles such as reactive oxygen species or metabolically modified xenobiotics/drugs. AF16 contains one cysteine residue in position 2 of SEQ.ID.NO. 2. AF-17, or any other disulfide comprising peptide according to the present application, such as but not limited to AF-7 and AF-9, is (are) thus protected against both oxidation of the sulfur, from reacting with other cysteines (disulfide formation), reacting with electrophiles and is thus more resilient against proteolytic activity.

Synthesis

Disulfide bonds are usually formed from the oxidation of sulfhydryl (—SH) groups. A variety of oxidants promote this reaction including air and hydrogen peroxide. Such reactions are thought to proceed via sulfenic acid intermediates. In the laboratory, iodine in the presence of base is commonly employed to oxidize thiols to disulfides. Alternatively, disulfide bonds in proteins are often formed by thiol-disulfide exchange. Such reactions are mediated by enzymes in some cases and in other cases are under equilibrium control, especially in the presence of a catalytic amount of base.

Many specialized methods have been developed for forming disulfides, for applications in organic synthesis and can be employed for producing the synthetic AF-17 or AF-7 or AF-9 or AF-7-based AF-disulfide peptides according to the present invention.

Figure 3A:
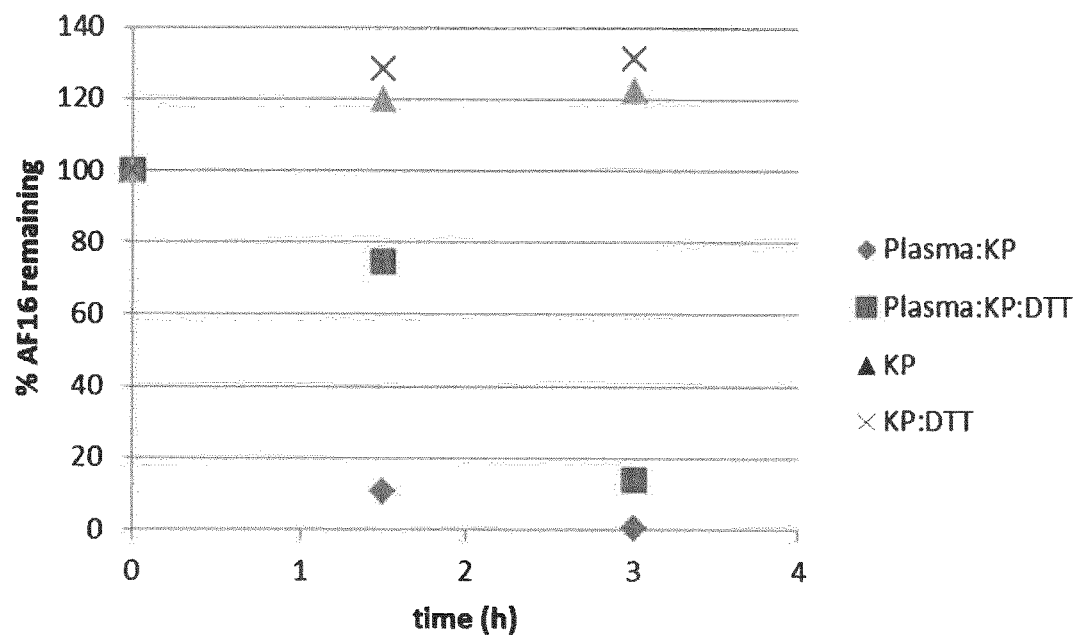
Figure 3B:
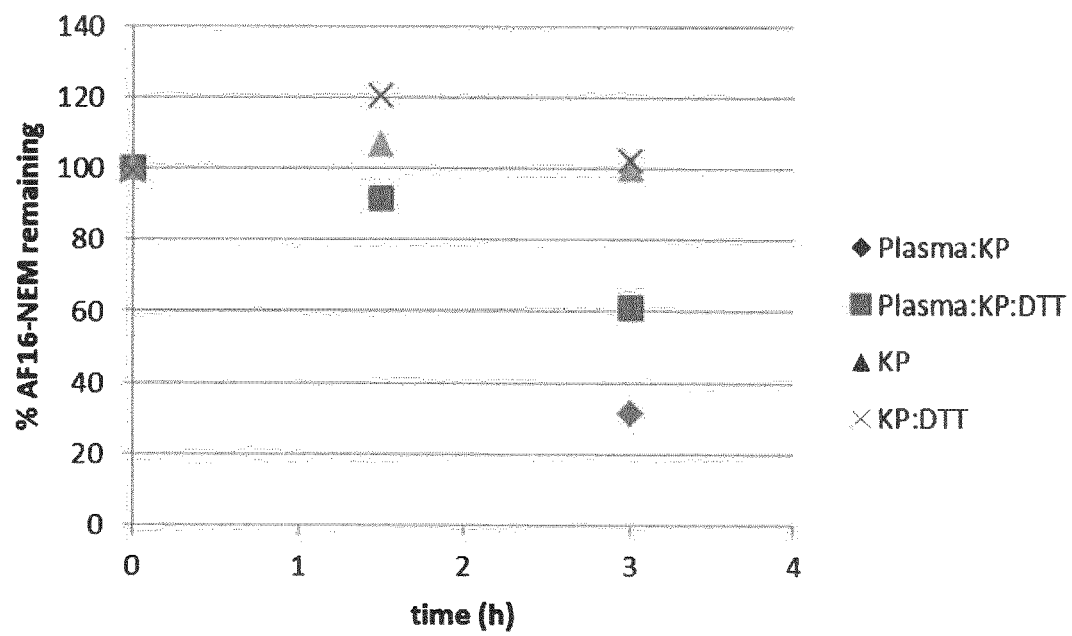

AF16 shows a high degree of sensitivity towards plasma as shown in FIG. 3A. The kinetics of degradation indicates an in vitro half-life ($t\frac{1}{2}$) of 0.4 h. AF-17 is anticipated to have an almost 5-fold higher stability, $t\frac{1}{2}=1.8$ h. AF16 is highly sensitive for enzymatic and chemical degradation in systemic circulation. AF-17 is more resilient towards enzymatic or chemical reactions as the cysteine moiety is modified.

Quantitative pilot experiments of AF16 during Caco-2 cell permeability experiments clearly showed a rapid disappearance of the peptide (not shown). It is well known that in the intestine, and as such at the apical side of Caco-2 cells, brush-border peptidases exist. The kinetics of degradation of AF16 is very rapid as described with a $t\frac{1}{2}$ of 8 min.

AF16 and the isotopically labelled peptide in similar quantity were incubated in plasma of rat and human as described in experiment 1. For analysis of fullscan MS data, a metabolite identification software from Sciex, Lightsight was used, which compares the incubated MS response to the quality control (QC) sample and assigns apparent peaks as metabolites with specific mass over charge (m/z) values. The largest metabolite peak areas were rank ordered and in some cases verified by MS/MS fragmentation. Skyline methodology was used to predict fragmentation of the identified peptides, but also aided in creating sensitive MRM methods so that low amounts could be monitored.

Table 6 lists the identified products and their relative amount at 30 min incubation. MS sensitivity, may differ and thus individual percentages may change. Upon reviewing the results, it was clear that based on the relative area of the identified peaks one metabolite was much larger than the other, designated M1 in table 6. However the mass pair identified (m/z 625/630) did not correspond to any catabolic products (expected proteolytic peptide bond cleavage). This pair is now identified as the cysteine disulfide of AF-16 (AF-17).

Medical Treatments

TBI

Traumatic brain injury (TBI) is a complex injury with a broad spectrum of symptoms and disabilities. Traumatic brain injury (TBI) is also known as intracranial injury, it occurs when an external force traumatically injures the brain. TBI can be classified based on severity, mechanism (closed or penetrating head injury), or other features (e.g., occurring in a specific location or over a widespread area). In the present context, TBI is also meant to include head injury, i.e. it can involve damage to structures other than the brain, such as the scalp and skull.

TBI is a major cause of death and disability worldwide, especially in children and young adults. Causes include falls, vehicle accidents, and violence. Brain trauma can occur as a consequence of a focal impact upon the head, by a sudden acceleration/deceleration within the cranium or by a complex combination of both movement and sudden impact. In addition to the damage caused at the moment of injury, brain trauma causes secondary injury, a variety of events that take place in the minutes and days following the injury. These processes, which include alterations in cerebral blood flow and the pressure within the skull, contribute substantially to the damage from the initial injury.

TBI can cause a host of physical, cognitive, social, emotional, and behavioral effects, and outcome can range from complete recovery to permanent disability or death.

In the present context, the following terms and definitions refer to the different injuries relating to/of TBI, all of which are treatable by administering an isolated recombinant and/or synthetically produced peptide, or a pharmaceutically active salt thereof, having equivalent functional activity, said peptide corresponding to a fragment of the antisecretory factor (AF) protein as shown in SEQ.ID.NO. 1 (AF) and/or a homologue thereof having equivalent activity, wherein said peptide at least comprises an amino acid sequence as shown in SEQ.ID.NO. 2 (AF-6) and a cysteine disulfide in amino acid position no. 1 of SEQ.ID.NO. 2, such as an amino acid sequence as shown in SEQ.ID.NO. 3 (AF-16) and a cysteine disulfide in amino acid position no. 2 of SEQ.ID.NO. 3, to a patient in need thereof: Closed Head Injury, Open Head Injury, Diffuse Axonal Injury, Contusion, Penetrating Trauma, and Secondary Injury.

The presently disclosed isolated recombinant and/or synthetically produced peptide, or a pharmaceutically active salt thereof, having equivalent functional activity, said peptide corresponding to a fragment of the antisecretory factor (AF) protein as shown in SEQ.ID.NO. 1 (AF) and/or a homologue thereof having equivalent activity, wherein said peptide at least comprises an amino acid sequence as shown in SEQ.ID.NO. 2 (AF-6) and a cysteine disulfide in amino acid position no. 1 of SEQ.ID.NO. 2, such as an amino acid sequence as shown in SEQ.ID.NO. 3 (AF-16) and a cysteine disulfide in amino acid position no. 2 of SEQ.ID.NO. 3, is particularly useful for treating and/or preventing secondary TBI, such as swelling and release of chemicals that promote inflammation and cell injury or death. This causes swelling in the brain which may increase the intracranial pressure and prevent the cerebrospinal fluid from draining out of the skull. This causes further increase in pressure and brain damage. If this is not controlled or prevented the brain can herniate (push through) the base of the skull and cause respiratory failure and death. The prevention of this secondary injury is the focus of the acute medical care after injury.

Thus the present invention in a presently preferred embodiment relates to the use of an isolated recombinant and/or synthetically produced peptide according to the present invention for the manufacturing of a pharmaceutical composition for treating and/or preventing secondary TBI injury. The present invention equally relates to the use of an isolated recombinant and/or synthetically produced peptide according to the present invention for treating and/or preventing secondary TBI injury, to an isolated recombinant and/or synthetically produced peptide according to the present invention for use in treating and/or preventing secondary TBI injury, as well as to a method of treating and/or preventing secondary TBI injury by administering to a patient in need thereof an isolated recombinant and/or synthetically produced peptide according to the present invention in an amount sufficient to treat and/or cure said patient and/or to prevent symptoms of TBI injury.

Secondary TBI Injury Includes:
Intracranial hemorrhage (bleeding inside the skull)
Brain swelling
Increased intracranial pressure (pressure inside the skull)
Brain damage associated with lack of oxygen
Infection inside the skull, common with penetrating trauma
Chemical changes leading to cell death
Increased fluid inside the skull (hydrocephalus)

Acquired Brain Injury—

Acquired Brain Injuries are injuries other than congenital, birth trauma, hereditary or degenerative. This includes traumatic brain injury. In the non-traumatic types of acquired brain injury, the brain is usually diffusely injured. These injuries are usually not included in traumatic brain injury but the symptoms span the same spectrum. Common causes are anoxia and hypoxia. These are lack of oxygen to the brain and insufficient oxygen to the brain. They can occur because of mechanical problems with breathing, with cardiac arrest or bleeding. Drugs and poisoning can also cause acquired traumatic brain injury. Carbon monoxide poisoning is an example of poisoning that may cause brain injury.

The presently disclosed isolated recombinant and/or synthetically produced peptide, or a pharmaceutically active salt thereof, having equivalent functional activity, said peptide corresponding to a fragment of the antisecretory factor (AF) protein as shown in SEQ.ID.NO. 1 (AF) and/or a homologue thereof having equivalent activity, wherein said peptide at least comprises an amino acid sequence as shown in SEQ.ID.NO. 2 (AF-6) and a cysteine disulfide in amino acid position no. 1 of SEQ.ID.NO. 2, such as an amino acid sequence as shown in SEQ.ID.NO. 3 (AF-16) and a cysteine disulfide in amino acid position no. 2 of SEQ.ID.NO. 3, is equally useful for treating and/or preventing Acquired Brain Injury.

Thus the present invention in a presently preferred embodiment relates to the use of an isolated recombinant and/or synthetically produced peptide according to the present invention for the manufacturing of a pharmaceutical composition for treating and/or preventing Acquired Brain Injury. The present invention equally relates to the use of an isolated recombinant and/or synthetically produced peptide according to the present invention for treating and/or preventing Acquired Brain Injury, to an isolated recombinant and/or synthetically produced peptide according to the present invention for use in treating and/or preventing Acquired Brain Injury, as well as to a method of treating and/or preventing Acquired Brain Injury by administering an isolated recombinant and/or synthetically produced peptide according to the present invention in an amount sufficient to a patient in need thereof.

Cancer

In one embodiment, the present invention relates to a method for treating cancer, such as, but not limited to, glioblastoma, characterized by administering an isolated recombinant and/or synthetically produced peptide, or a pharmaceutically active salt thereof, having equivalent functional activity, said peptide corresponding to a fragment of the antisecretory factor (AF) protein as shown in SEQ.ID.NO. 1 (AF) and/or a homologue thereof having equivalent activity, wherein said peptide at least comprises an amino acid sequence as shown in SEQ.ID.NO. 2 (AF-6) and a cysteine disulfide in amino acid position no. 1 of SEQ.ID.NO. 2, such as an amino acid sequence as shown in SEQ.ID.NO. 3 (AF-16) and a cysteine disulfide in amino acid position no. 2 of SEQ.ID.NO. 3, to a patient in need thereof. Said method can in one embodiment of the present invention be used to facilitate an optimized drug uptake and delivery of a further pharmaceutical substance.

Said method for treating a mammalian suffering from cancer, such as, but not limited to, glioblastoma, can in a presently preferred embodiment comprise feeding a food, food stuff and/or food supplement to said patient and thereby inducing endogenous production of AF for facilitating an optimized drug uptake and delivery of a further pharmaceutical substance.

Said pharmaceutical substance and/or formulation is in the present context selected from the group consisting of anticancer drug, antitumor drug, radiation therapy, immunological substances and/or cells and antibiotic substance, a drug targeting posttraumatic injury, a drug targeting neurodegeneration, and a drug against inflammatory conditions. Said further pharmaceutical substance can be in the form of nano particles and/or formulations thereof in the treatment of cancer, such as, but not limited to, glioblastoma (a GBM tumor).

Hereinafter, the embodiments of the present invention will be described in detail. It is to be noted that the embodiments individually disclosed below are examples of the isolated or synthetic peptide and the intended use of the peptide. The present invention is not limited to these examples.

Compartment Syndrome

Furthermore, the present invention in one embodiment relates to the use of an isolated recombinant and/or synthetically produced peptide according to the present invention for the manufacturing of a pharmaceutical composition for treating and/or preventing Compartment Syndrome. The present invention equally relates to the use of an isolated recombinant and/or synthetically produced peptide according to the present invention for treating and/or preventing Compartment Syndrome, to an isolated recombinant and/or synthetically produced peptide according to the present invention for use in treating and/or preventing Compartment Syndrome, as well as to a method of treating and/or preventing Acquired Brain Injury by administering an isolated recombinant and/or synthetically produced peptide according to the present invention in an amount sufficient to a patient in need thereof.

In one embodiment, the present invention relates to a method for treating and/or preventing Compartment Syndrome or symptoms thereof, characterized by administering an isolated recombinant and/or synthetically produced peptide, or a pharmaceutically active salt thereof, having equivalent functional activity, said peptide corresponding to a fragment of the antisecretory factor (AF) protein as shown in SEQ.ID.NO. 1 (AF) and/or a homologue thereof having equivalent activity, wherein said peptide at least comprises an amino acid sequence as shown in SEQ.ID.NO. 2 (AF-6) and a cysteine disulfide in amino acid position no. 1 of SEQ.ID.NO. 2, such as an amino acid sequence as shown in SEQ.ID.NO. 3 (AF-16) and a cysteine disulfide in amino acid position no. 2 of SEQ.ID.NO. 3, to a patient in need thereof. Said method can in one embodiment of the present invention be used to facilitate an optimized drug uptake and delivery of a further pharmaceutical substance.

EXPERIMENTAL SECTION

Example 1

The effect of the peptide fragment of antisecretory factor protein (AF16) is fairly well studied in various pharmacological setups by several groups. The majority of studies have focused on the pharmacologic/physiologic effect of the protein or peptide. There are however fewer reports that deal with the pharmacokinetic viewpoint of AF16. Thus, all the testing in various matrices has assumed that AF, or presumably the added peptide fragment thereof, is the molecular species that is causing the effect. Previous studies in other labs have in fact indicated that AF or AF16 is sensitive to degradation in e.g. human or rodent plasma but no detailed investigation have been performed.

This experiment summarizes efforts in understanding the in vitro pharmacokinetics and the molecular fate of the AF16 peptide in both human pooled plasma but also in presence of Caco-2 cells, which is commonly used in AF16 pharmacological studies.

Materials and Methods

Materials

Solid material of AF16 and the stable isotopically labeled (SIL) AF16 IS was provided by Jan Bruhn at Lantmännen. According to information provided by Ewa Johansson at Sahlgrenska Hospital the peptide is approximately 70% in purity, other components being 4× trifluoroacetic acid (TFA) and unknown x H2O. However for sake of simplicity all concentrations regarding the peptide are considered to be 100%. This assumption does not influence the results presented herein since they are on a relative basis. All other chemicals and consumables were from common commercial sources.

Alkylation and Oxidation of AF16

To test for oxidation of AF16 a 50% hydrogen peroxide (H2O2) solution was used. 2 µl H2O2 was added (35 mM final conc.) to a 1 ml solution of 15 µM AF16 in 0.1 M ammonium bicarbonate. Immediately after mixing, the solution was injected (direct infusion) to the mass spectrometer (MS) to look for oxidation products. Only the oxidative end-product was detected, the sulfonic acid, of which a sensitive multiple reaction method (MRM) was created (table 1). In a simultaneous experiment, adding a surplus of dithiothreitol (DTT), showed that DTT protected against the oxidation. The N-ethyl maleimide (NEM) alkylated variant of AF16 (AF16-NEM) was produced by mixing 10 µl 0.1 M NEM with 250 µl 2 mg/ml AF16 in PBS in a HPLC glass vial yielding approximately a 1 mM solution. The sample was left standing, sealed, at ambient temperature for 30 min before MS analysis. After 30 min less than 5% of AF16 was remaining and a sensitive MRM method of AF16-NEM was created (table 1).

AF16 Stability in Human Plasma and Caco-2 Cells

Test of AF16 and AF16-NEM stability in plasma was performed using pooled human plasma (4 donors, two female+two male) in HPLC glass vials at 37° C. (20 µM incubation conc.). Four different matrices were tested: Plasma: isotonic 67 mM potassium phosphate pH 7.4 (KP) (1:1), plasma:KP+0.1 mM DTT, KP and KP+0.1 mM DTT. Incubation times were 0, 1.5 and 3 h. At the indicated times a 50 µl aliquot was extracted and quenched/precipitated in 150 µl ice-cold methanol and frozen until analysis. Relative quantification was performed UPLC-MS/MS.

Investigation of the fate of AF16 in the presence of Caco-2 cells was performed on three separate occasions. Firstly, a quantitative measurement was performed using MRM methodology (table 1) over 0, 15, 30 and 60 min. Here, AF16 or its possible sulfonic acid metabolite was monitored both in the apical and in the basolateral compartment (not shown). The second experiment was a qualitative determination of the fate of AF16 during a 60 min incubation. 50 µM AF16 in HBSS buffer was incubated at the apical side of the Caco-2 cell monolayer and 100 μl aliquots was extracted at 5, 10, 20, 30 and 60 min. The sample was placed on a 96-well plate containing 100 μl MeCN/H2O. The plate was sealed and frozen until full-scan UPLC-MS analysis (see below and table 2). The third experiment was a mirror of the second and the only difference was that a HBSS solution of AF16:AF16 IS (1:1) was used, to aid in the structure elucidation.

Analytical Procedures

All samples from the different assays were analyzed by UPLC-MS/MS. The following system was used, a Waters XEVO TQ triple-quadrupole mass spectrometer (electrospray ionization, ESI) coupled to a Waters Acquity UPLC (VVaters Corp.). For chromatographic separation a general gradient was used (1% mobile phase B to 50% over 3 min total run) on a C18 BEH 1.7 μm column 2×100 mm (VVaters Corp.). Mobile phase A consisted of 0.05% TFA and mobile phase B 100% acetonitrile. The flow rate was 0.5 ml/min. 5 μL of the sample were injected and run with the mass spectrometric settings reported in table 1. In the full-scan MS analysis the same chromatographic settings was used except that 10 μl was injected (full loop). The MS was set to scan for ions in the 100-400 or 400-700 m/z window using the cone voltage in table 1. For daughter scan analysis of selected parent ions in table 2 the collision energy was stepped between 10, 20 and 40 V. The parent ion, suggested charge and retention time of AF16 and found metabolites are listed in table 2.

TABLE 1

MRM MS specific settings used for detection. Product ions in bold used for quantitative analysis.

| Compound | ESI (+/−) | m/z (parent) | m/z (product) | Cone Voltage (V) | Collision energy (V) |
|---|---|---|---|---|---|
| AF16 | + | 586.0 | 784.2/734.7/490.2 | 26 | 16/20/18 |
| AF16 IS | + | 590.6 | 791.2/741.6/494.7 | 26 | 16/20/18 |
| AF16 sulfonic acid | + | 601.9 | 758.5/808.1/836.7 | 20 | 18/14/14 |
| AF16 NEM | + | 627.7 | 797.2/846.8/531.8 | 32 | 20/20/20 |

TABLE 2

Molecular ion m/z values and chromatographic retention time found in incubations of AF16 with Caco-2 cells.

| Name | m/z (Da) | Charge (xH) | Retention time (min) |
|---|---|---|---|
| AF16 | 586 | +3H | 2.14 |
| M1 | 601 | +2H | 2.19 |
| M2 | 645 | +1H | 2.21 |
| M3 | 518 | +3H | 2.14 |
| M4 | 402 | +1H | 2.25 |
| M5 | 472 | +2H | 2.22 |
| M6 | 626 | — | 2.13 |
| M7 | 565 | +2H | 1.94 |
| M8 | 418 | — | 1.93 |
| M9 | 479 | — | 2.11 |

Results

Alkylation and Oxidation of AF16

Cysteine residues are among the most chemically involved amino acids, participating typically in redox chemical reactions but also as a nucleophile against reactive electrophiles such as reactive oxygen species or metabolically modified xenobiotics/drugs. AF16 contains one cysteine residue so it was important to test if sensitivity towards oxidation or other modification occurs in vitro. At first, oxidation of AF16 with hydrogen peroxide was performed in order see if it was possible to create analytical MS methods of the possible sulfenic, sulfinic and sulfonic acid derivatives (FIG. 1). Hydrogen peroxide was proven to be a too strong oxidizing reagent to allow detection of the lower order species and thus only method for the sulfonic acid analog was created.

Figure 2:
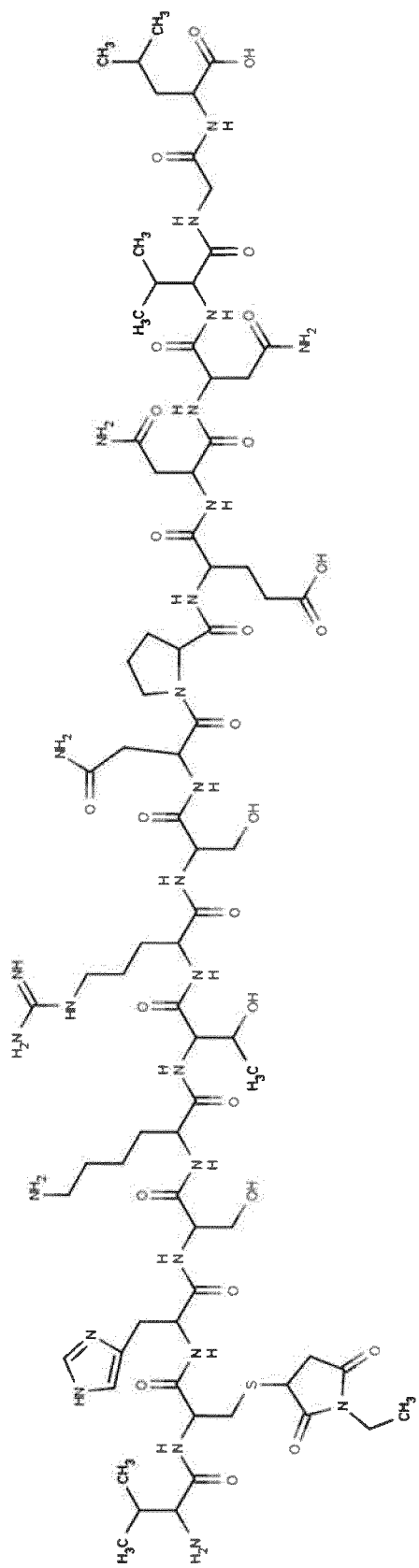

To further explore the role of the cysteine in subsequent experiments an alkylated variant was created using the S-alkylating reagent N-ethyl maleimide (NEM) (FIG. 2). NEM modified AF16 is thus protected against both oxidation of the sulfur, from reacting with other cysteines (disulfide formation), reacting with electrophiles and presumably more resilient against proteolytic activity, being an unnatural amino acid.

AF16 Stability in Human Plasma.

AF16, the stable isotope labeled (SIL) AF16 and the alkylated analog AF16-NEM were incubated at 1 μM in human plasma: 0.1M potassium phosphate pH 7.4 (KP) (1:1), human plasma: KP (1:1)+1 mM DTT, KP or KP+1 mM DTT over 3 h at 37° C. to investigate stability. KP was included to provide buffer capacity to the plasma and to not confuse the results with pH related effects. The results are shown in FIG. 3.

AF16 shows a high degree of sensitivity towards plasma as shown in FIG. 3A. The kinetics of degradation indicates an in vitro half-life (t½) of 0.4 h. Inclusion of DTT seems to have a protective effect which increases the t½ to 1.1 h. Interestingly the unnatural AF16 analog (FIG. 3B) has an almost 5-fold higher stability, t½=1.8 h. Also here DTT imposes a protective effect, t½=4.2 h. These results indicate AF16 to be highly sensitive for enzymatic and chemical degradation in systemic circulation. It also shows that AF16 is more resilient towards enzymatic or chemical reactions if the cysteine moiety is modified. The effect of DTT with both compounds is more difficult to understand but most likely this reflects that DTT protects against general oxidation reactions, such as formation of carbonyl products, e.g. threonine, lysine, arginine and proline, all present in AF16.

Full-scan LC-MS analysis of the 3 h incubations of AF16, SIL-AF16 and AF16-NEM revealed a few interesting results, see FIG. 4. Two distinct degradation products were found, cleavage at the 5th peptide bond (lysine and threonine) and at the 10th bond (proline and glutamate) yielding the theoretical fragments VCHSK-TRSNP (SEQ ID NO: 15), TRSNP-ENNVGL (SEQ ID NO: 10) and ENNVGL (SEQ ID NO:11). The fragments TRSNP-ENNVGL (SEQ ID NO: 10) and ENNVGL (SEQ ID NO: 11) were detected by LC-MS but not VCHSK-TRSNP (SEQ ID NO: 15). Presumably the undetected fragment underwent further degradation during the incubation. Interestingly, in the incubation with AF16-NEM, no apparent proteolysis occurred at position five, indicating that proteases acting towards the N-terminus are excluded, e.g. aminopeptidases.

AF16 Stability with Caco-2 Cells

Quantitative pilot experiments of AF16 during Caco-2 cell permeability experiments clearly showed a rapid disappearance of the peptide (not shown). It is well known that in the intestine, and as such at the apical side of Caco-2 cells, brush-border peptidases exist. To further investigate this, a separate experiment was designed. Caco-2 cells were exposed at the apical side to 50 μM AF16, with or without a protease inhibitor cocktail, and were sampled over 1 h. The results on AF16 degradation are shown in FIG. 5.

Figure 7:
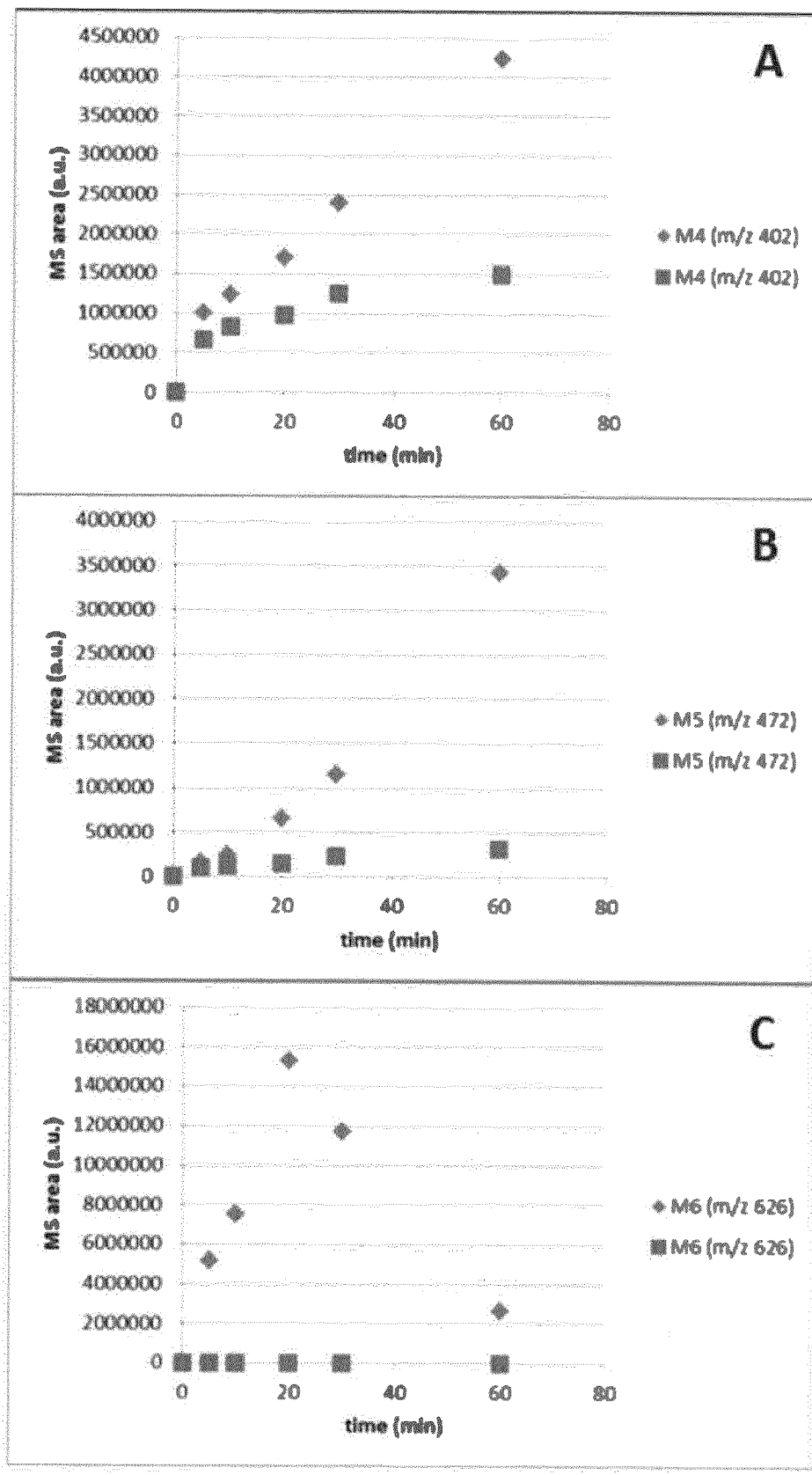
Figure 8:
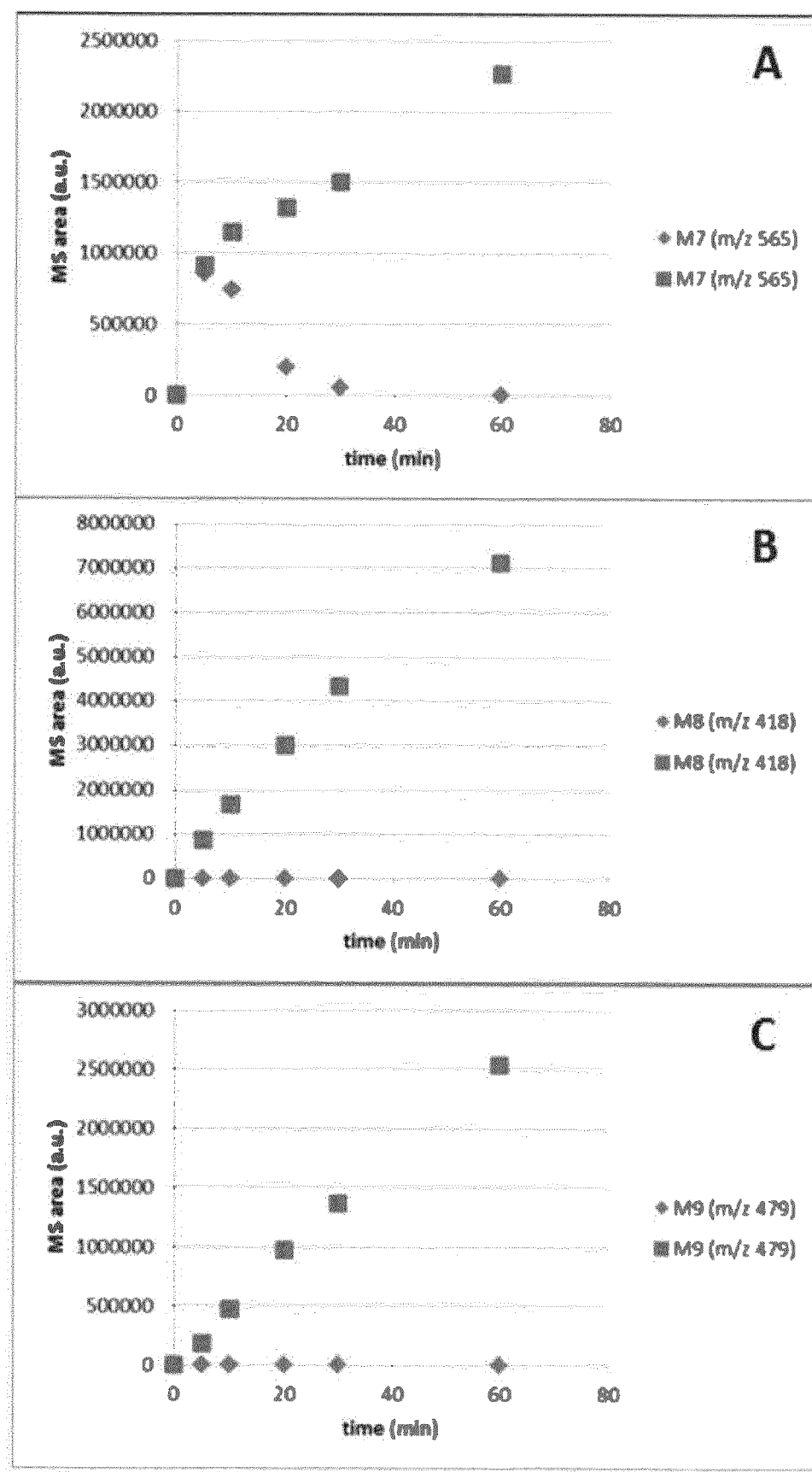

The kinetics of degradation of AF16 is very rapid as described with a t½ of 8 min. The inhibitor cocktail significantly slows down the degradation (t½=57 min) but not completely indicating complicated kinetics. LC-MS analysis was pursued in order to understand the molecular fate of AF16. In the incubations with or without inhibitors several new metabolites were detected in comparison to the plasma stability experiment. However this can depend on the higher incubation concentration used. FIG. 6-8 show the formation kinetics of the metabolites M1-M9 over the experimental time and FIG. 9 shows the tentatively determined structures to these products.

Table 3 shows the relative amounts of the individual molecular species, ±inhibitor cocktail, after 30 and 60 min, respectively. The apparently major metabolites (>10%) are indicated in bold numbers. It is however important mentioning when doing such comparisons as in table 3 that we assume that all the individual ions have similar MS sensitivity. All the identified products relate to cleavages at specific peptide bonds. The suggested amino acid compositions are shown in table 4.

In absence of the inhibitor cocktail, three clear metabolites dominate after 30 min incubation, M1, M3 and M6. After 60 min incubation both M3 and M6 decline, whereas M1 continues to increase linearly (FIGS. 6A/C and 7C). Looking at the suggested pathways in FIG. 9, it is reasonable to assume that further N-terminal peptide cleavage of M3 results in M1. Without knowing the structure of M6 and its relatively rapid decline after 20 min, this may also indicate that M6 contributes to the formation of M1. The other metabolites are suggested to be further degradation products of M1 but could of course be formed in a more direct manner as well, by a slower pathway.

TABLE 3

Tentative amounts (%) of the respective molecular species at 30 or 60 min incubation with Caco-2 cells. (+/−peptidase inhibitor cocktail)

| | AF16 | M1 | M2 | M3 | M4 | M5 | M6 | M7 | M8 | M9 |
|---|---|---|---|---|---|---|---|---|---|---|
| (−) inhib. | | | | | | | | | | |
| 30' | 6 | 20 | 3 | 38 | 5 | 2 | 25 | 0.1 | 0 | 0 |
| 60' | 1 | 41 | 10 | 24 | 9 | 8 | 6 | 0 | 0 | 0 |
| (+) inhib. | | | | | | | | | | |
| 30' | 79 | 1 | 1 | 2 | 2 | 0.4 | 0 | 3 | 8 | 3 |
| 60' | 63 | 2 | 1 | 4 | 3 | 0.7 | 0 | 4 | 15 | 5 |

The inhibitor cocktail consisted of three inhibitors of proteolytic enzymes, Bestatin (aminopeptidase), Diprotin A (dipeptidylpeptidase IV) and Captopril (angiotensin converting enzyme, a carboxypeptidase). It is interesting to see that due to inhibition of these enzymes, the formation of M1, M3 and M6 is effectively minimized. Moreover, the theoretical product M7, shown in FIG. 4, 9 and table 4, is formed in a relatively linear manner and seems to be stabilized by the inhibitors. This is in agreement with inhibition of N-terminal acting proteases. FIG. 8A suggests M7 to be formed very rapidly initially without inhibitors but is likely efficiently further metabolized. Although relatively small, the major metabolites M8 and M9 have not been identified as of yet. It is quite possible that these two metabolites stem from more complicated chemistry than peptide bond cleavage as mentioned above. However, in order to try to understand the structure of the unknown metabolites M6, M8 and M9 and to verify the already structurally assigned, an additional experiment was performed using the SIL labeled AF16. From this experiment, one could however not extract any more information part from the fact that M6 contains a SIL amino acid and M8 and M9 do not. This however needs to be further explored.

TABLE 4

Suggested amino acid composition of tentatively identified peptides.

| Name | m/z (Da) | Amino acid number | Amino acid composition |
|---|---|---|---|
| AF16 | 586 | 1-16 | VCHSK TRSNP ENNVG L |
| M1 | 601 | 6-16 | TRSNP ENNVG L |
| M2 | 645 | 11-16 | ENNVG L |
| M3 | 518 | 3-16 | HSK TRSNP ENNVG L |
| M4 | 402 | 13-16 | NVG L |
| M5 | 472 | 8-16 | SNP ENNVG L |
| M6 | 626 | — | — |
| M7 | 565 | 1-10 | VCHSK TRSNP |
| M8 | 418 | — | — |
| M9 | 479 | — | — |

Permeability of either AF16 or any of the detected metabolites was also monitored at the basolateral side after 60 min incubation time with the Caco-2 cells. No metabolites were however found in this experiment except for M8, which gave a distinct peak in the inhibited incubation.

Conclusions and Future Studies

A number of important in vitro experiments have been performed in order to further understand the in vitro pharmacokinetics of AF16.

AF16 most likely adsorbs to e.g. polystyrene surfaces. However, the described countermeasures did not show an effect and it is difficult to interpret how severe it is. At higher concentration, >1 µM, the effect is not apparent and thus in our incubations the effect is most likely minor.

The current studies have shown that AF16 peptide degrades to several peptide products in the presence of both human plasma and Caco-2 cells.

The degradation is very rapid in both matrices and indicates a similar metabolic pathway, yielding M1 as a major, linearly formed and apparent stable product (cleavage at the 5th peptide bond (lysine and threonine)).

The involvement of brush border peptidases is proven by a strong effect of the inhibitor cocktail, which increases the in vitro $t_{1/2}$ from 8 to 55 min. The change in metabolic pattern in the presence of protease inhibitors is interesting but the currently unknown metabolites (M8, M9) are most likely not formed to a significant degree in the absence of inhibitors.

Protection of the cysteine at position 2 with N-ethyl maleimide greatly stabilizes the peptide in human plasma. Most likely due to removal of activity of aminopeptidases.

Taking these results together strongly suggests that the in vitro pharmacokinetics of AF16 is complex and carefully needs to be balanced and interpreted to the pharmacologic effect that's been observed under various conditions. It is apparent that AF16 is rapidly disappearing in vitro after a short incubation time with Caco-2 cells. Further, a few metabolites are formed very rapidly at a rate that parallels AF16 disappearance. It is quite possible that AF16 and the metabolites act against the same target with similar efficiency this will be proven in a functional assay.

Example 2

AF16: Plasma In Vitro Stability and Metabolic Fate

Introduction

This experiment summarizes the latest findings on inter-species (human, mouse, rat and dog) plasma kinetics and the qualitative catabolism/metabolism of AF16 in human and rat plasma.

Materials and Methods

Materials

Solid material of AF16 and the stable isotopically labeled (SIL) AF16 IS was provided by Lantmännen AB. According to information provided by Ewa Johansson at Sahlgrenska Hospital, the peptide is approximately 70% in purity, other components being 4× trifluoroacetic acid (TFA) and unknown x H2O. However, for the sake of simplicity, all concentrations regarding the peptide are considered to be 100%. This assumption does not influence the results presented herein, since they are compared on a relative basis. Human pooled plasma (4 donors, 2 male and 2 female, nonsmokers) were obtained from the academic hospital. Animal plasma was from Novakemi AB. All other chemicals and consumables were from common commercial sources.

Test of Plasma Percipient

To optimize the MS sensitivity of AF16, the most common protein precipitation agents with apparent similar efficiency were tested. The plasma matrix consisted of 1:2 (plasma: isotonic potassium phosphate buffer) (pH 7.4) and was precipitated in HPLC glass vials with either: 1:3 (plasma acetonitrile (MeCN)), 1:4 (plasma: methanol (MeOH)), 1:3 (plasma: zinc sulfate (ZnSO4: 5 M NaOH) (10% w/v)) and 1:3 (plasma: trichloroacetic acid (TCA) (10% w/v)) (Polson et al, 2003). The sample was spiked with a 10 μM (final concentration) 1:2 mixture of AF16 and the isotopic labelled AF16 (AFIS). The samples were sealed and centrifuged at 3500 rpm. After centrifugation, the supernatants were analyzed by UHPLC-MS/MS (see below). The identical samples were injected three times at different time points to probe the peptide stability with a given precipitant in the auto sampler at 10° C.

AF16 Stability, Kinetics and Metabolite Identification in Human and Rat Plasma

All the incubations of the plasma samples utilized a mixture of AF16 (stock solution 1 mM in MeCN:H$_2$O) and AFIS (stock solution 0.9 mM in MeCN:H$_2$O) 1:2, this to aid in structural interpretation of metabolic or catabolic products. The compound mixture was always pipetted to the bottom of the vial prior to the addition of any other solvent. The stability in plasma was performed using pooled human pooled plasma, Wistar Rat plasma, CD-1 mouse plasma and Beagle dog plasma, in sealed HPLC glass vials at 37° C. (10 μM incubation conc.). Incubation times were in general between 0 (QC sample) and 2 h. At each time point an aliquot was taken and reaction was stopped with the selected precipitant incl. dithiothreitol (DTT) (1 mM final conc.). Relative quantification (compared to QC) was performed using UHPLC-MS/MS (see below). Metabolite identification was performed using multiple reaction monitoring (MRM, Skyline predicted MRM)), Lightsight software (Sciex) enhanced MS scan (EMS), enhanced product ion scan (EPI) and enhanced resolution scan (ERS).

Analytical Procedures

All samples from the different assays were analyzed by UHPLC-MS/MS with utilization of the linear ion trap for the EMS, ERS and EPI scan. The following system was used; Sciex QTRAP 6500 triple-quadrupole mass spectrometer (electrospray ionization, ESI) with a linear ion trap coupled to an Agilent 1290 UHPLC. For chromatographic separation a general gradient was used (0% mobile phase B to 90% over 5-15 min total run) on a C18 HSS T3 1.8 μm column 2×50 mm (Waters Corp.). Mobile phase A consisted of 0.05% TFA/0.05% formic acid and mobile phase B 100% acetonitrile 0.05% TFA/0.05% formic acid. The flow rate was 0.5 ml/min. 10 μL of the sample were injected and run with the mass spectrometric settings reported in table 5.

TABLE 5

MRM MS specific settings used for detection of AF16 and metabolites.

| Compound | ESI (+/−) | m/z (parent) | m/z (product) | Declustering potential (V) | Collision energy (V) |
|---|---|---|---|---|---|
| AF16 | + | 586.0 | 734.7 | 73.8 | 28.4 |
| AF16 IS | + | 590.6 | 741.6 | 73.8 | 27.4 |
| CHSKTRSNPENNVGL + 3b12 + 2light | + | 552.6 | 684.8 | 73.8 | 28.4 |
| CHSKTRSNPENNVGL + 3b12 + 2heavy | + | 554.6 | 687.8 | 73.8 | 27.4 |
| SNPENNVGL + 2b6light | + | 472.2 | 656.3 | 71.4 | 26.7 |
| SNPENNVGL + 2b6heavy | + | 475.2 | 662.3 | 65.5 | 24.9 |
| RSNPENNVGL + 2b7light | + | 550.3 | 812.4 | 65.5 | 23.9 |
| RSNPENNVGL + 2b7heavy | + | 553.3 | 818.4 | 65.5 | 23.9 |
| TRSNPENNVGL + 2b8light | + | 600.8 | 913.4 | 71.2 | 28.7 |
| TRSNPENNVGL + 2b8heavy | + | 603.8 | 919.4 | 74.9 | 29.5 |
| NPENNVGL + 2b5light | + | 428.7 | 569.2 | 74.9 | 32.5 |
| NPENNVGL + 2b5heavy | + | 431.7 | 575.2 | 74.9 | 30.5 |
| ENNVGL + 1b3light | + | 645.3 | 358.1 | 62.4 | 23.3 |
| SKTRSNPENNVGL + 2b6light | + | 708.4 | 674.4 | 78.2 | 30.1 |
| SKTRSNPENNVGL + 2b6heavy | + | 711.4 | 674.4 | 78.2 | 28.1 |
| HSKTRSNPENNVGL + 2b7light | + | 776.9 | 811.4 | 82.8 | 34.4 |
| HSKTRSNPENNVGL + 2b7heavy | + | 779.9 | 811.4 | 82.8 | 34.4 |
| VC[SCC]HSKTRSNPENNVGL + 3b13 + 2light | + | 625.3 | 793.8 | 87.8 | 36.8 |
| VC[SCC]HSKTRSNPENNVGL + 3b13 + 2heavy | + | 630.0 | 800.9 | 76.7 | 30.6 |
| C[SCC]HSKTRSNPENNVGL + 3b13 + 2light | + | 592.3 | 744.4 | 75 | 35 |
| C[SCC]HSKTRSNPENNVGL + 3b13 + 2heavy | + | 594.4 | 747.4 | 75 | 35 |

Results and Discussion

Impact of Plasma Protein Precipitate on AF16 MS-Sensitivity and UHPLC Chromatography Due to the complexity of the plasma matrix, it was important to test how AF16 chromatography and mass spectrometry (MS) sensitivity responds to different protein precipitation methods. The chosen precipitants are commonly applied and have been shown to be of similar efficiency. The results are shown in FIGS. 10 and 11.

FIG. 10 shows the results of repeated injection of the same sample three times over 20 h. It is clear that TCA and MeCN show good apparent stability over time. A slight disappearance is noted with ZnSO4 at 20 h. A significant loss over time is shown with MeOH. It is likely that AF16 is stable with MeOH but the loss stems from peptide precipitation since it is known that peptides may have limited solubility in alcoholic mixtures. Further tests are to be performed.

FIG. 11 shows a diagram of the data acquired above in comparison to each other in terms of MS-intensity (ion counts). TCA precipitation showed the strongest signal and was set as the reference. It is clear that the nonorganic methods fall behind, most likely due to co-eluting suppressing ions. The two methods with best stability (TCA and MeCN) show over 500-fold difference in sensitivity, thus for the continued studies, TCA was chosen to be used throughout the study.

Plasma Stability of AF16

The relative stability of AF16 in different species is shown in FIG. 12. Irrespective of species, AF16 is rapidly disappearing with an in vitro half-life ($t_{1/2}$) less than or equal to 10 min. Thus, it is of utmost importance to determine the molecular fate of the peptide in order to understand the pharmacokinetic basis of any pharmacological action.

Molecular Fate of AF16 in Human and Rat Plasma

AF16 and the isotopically labelled peptide in similar quantity were incubated in plasma of rat and human as described above. For analysis of full scan MS data, the metabolite identification software from Sciex, Lightsight, was used, which compares the incubated MS response to the quality control (QC) sample and assigns apparent peaks as metabolites with specific mass over charge (m/z) values. The software is currently not optimal to use with multi-charged compounds such as peptides so the hit-rate of metabolite detection is fairly high and manual assessment of each found peak had to be performed. The largest metabolite peak areas were then rank ordered and in some cases verified by MS/MS fragmentation. Skyline methodology was used to predict fragmentation of the identified peptides, but also aided in creating sensitive MRM methods so that low amounts could be monitored.

Table 6 lists the identified products and their relative amount at 30 min incubation. It must however be emphasized that this comparison assumes that each product has the same MS sensitivity, which may differ and thus individual percentages may change. Upon reviewing the results it was quite clear that based on the relative area of the identified peaks one metabolite was much larger than the others, designated M1 in table 6. However, the mass pair identified (m/z 625/630) did not correspond to any catabolic products (expected proteolytic peptide bond cleavage). This pair is now identified as the cysteine disulfide of AF16.

TABLE 6

Relative area % of identified metabolites in human and rat plasma.

| | | % of QC area at 30 min incubation time | |
|---|---|---|---|
| Name | Peptide sequence | Human | Rat |
| AF16 | VCHSKTRSNPENNVGL | 1 | 4 |
| M1 | VC(C)HSKTRSNPENNVGL | 17 | 24 |
| M2 | CHSKTRSNPENNVGL | 0.5 | 0.3 |
| M3 | HSKTRSNPENNVGL | 0.9 | 0.4 |
| M4 | SKTRSNPENNVGL | 2.2 | 0.6 |
| M5 | TRSNPENNVGL | 3.5 | 1.1 |
| M6 | RSNPENNVGL | 0.8 | 0.1 |
| M7 | SNPENNVGL | 1.6 | 0.8 |
| M8 | NPENNVGL | 0.7 | 0 |
| M9 | ENNVGL | 4.3 | 1.4 |

FIG. 13 shows the relative kinetics of the identified metabolites and it is apparent that the cysteine disulfide M1 is formed similarly, in both rate and amount, in human and rat plasma, indicating that rat may be a good model for pharmacological studies. The greatest disparity between human and rat is the formation of M9, which is formed linearly over time in human but to a very low extent in rat. One explanation to this could be that human plasma proteolytic activity of the smaller fragments is higher than in the rat plasma. One metabolite (M10) with an m/z pair of 592.3/594.4 (not shown in table 6/FIG. 13) remained puzzling and was first understood after MS/MS studies and ERS mode scan (FIG. 14). ERS showed that it was triple charged on the $^{13}$C isotope pattern (0.3 Da step between isotopic peaks) and agreed with a M2 disulfide product. M2 is formed in apparent low amounts but this formation could be obscured by an efficient cysteine oxidation, forming the disulfide. Alternatively M10 is formed from M1 but that is less likely. Simple cleavage of the N-terminal Valine is quite surprising (forming M2) since most N-terminal acting peptidases cut two amino acids at a time and it is, to our knowledge, rare that a peptidase would act so close to the disulfide and form M10.

To further verify that indeed these products, M1 and M10, were disulfides, a reaction mixture was incubated with the cysteine selective alkylating agent N-ethyl maleimide which confirmed no reaction with these metabolites (not shown).

The kinetics shown in FIG. 13 was surprising given the fact that DTT was used in the quenching solution with TCA, although it is likely that the reducing capability of DTT is lowered in acidic conditions. It was therefore tested if the same pattern occurred when using a neutral precipitant ZnSO4 (without NaOH). This precipitation method is not as efficient but would hopefully give more information on the formation of the major disulfide products. The results are shown in FIG. 15.

From FIG. 15 and comparing to FIG. 13 it is clear that no large difference is indicated and it is also very surprising how resilient the M1/M10 disulfide is against DTT reduction.

Conclusions and Future Studies

A number of important in vitro experiments have been performed in order to further understand the in vitro pharmacokinetics of AF16 and how it may translate to the in vivo situation.

1. Trichloroacetic acid has been identified as the optimal choice for removing the plasma proteins in the incubation mixture and maintaining a good MS sensitivity and chromatography.
2. AF16 is known to be rapidly degrading in plasma from earlier studies. This investigation further validates this but also shows that the rate is similar between different species.
3. The apparent major metabolic fate in plasma, of both rat and human, is shown to be rapid disulfide formation of AF16. This action, being reversible, clearly protects AF16 from rapid peptidase degradation, which has been shown earlier with N-ethyl maleimide stabilization which is less reversible. This can be viewed as a protective function which enables AF16 to reach its target intact to a much higher degree.
4. The M1/M10 disulfide is surprisingly resilient against DTT reduction.

Example 3

(AF-17) is synthesized to be able to accurately quantify in vitro/in vivo but also to study the in vitro pharmacokinetic properties in general and to be used in pharmacological studies.

Biological activity of AF-17—The antisecretory activity was measured in a rat intestinal loop model previously described (Lange, S. (1982) FEMS Microbiol. Lett. 15, 239-242). A jejunal loop was challenged with 3 pg of cholera toxin. Different doses of synthetically produced AF-17, AF-16 or control (=no peptide, only buffer (XY)) was injected either intravenously or intramuscular, before challenge with cholera toxin. The weight of the accumulated fluid in the intestinal loop (mg/cm (mg/ml)) was recorded after five hours. Each AF preparation was tested in at least six rats. Fisher's PLSD was used for statistical analysis of the data.

Biological activity of AF-17—The biological activity of the AF-17 was tested in a rat model. The capacity of the AF-17 to inhibit intestinal fluid secretion when injected intravenously or intramuscular 20-30 sec before intestinal challenge with cholera toxin is shown in table 7. In control animals injected with buffer only, the cholera toxin caused a pronounced secretion, 390 mg fluid per cm intestine.

AF-17 caused dose-dependent inhibition of the cholera secretion which was significantly different from the response to the buffer ($p<0.001$, $n=6$).

TABLE 7

| AF-17 Administration mode | Mean ± SEM | N | Significance |
|---|---|---|---|
| Control | 390 ± 5 | 12 | — |
| 10 µg intravenously | 166 ± 9 | 6 | Vs control, $p < 0.001$ |
| 1 µg intravenously | 190 ± 17 | 6 | Vs control, $p < 0.001$ |
| 20 µg intramuscular | 152 ± 14 | 6 | Vs control, $p < 0.001$ |

TABLE 8

| AF-16 Administration mode | Mean ± SEM | N | Significance |
|---|---|---|---|
| Control | 413.5 ± (?) | 8 | — |
| 0.1 µg intravenously | 168 ± (?) | 8 | VCs control, $p < 0.001$ |
| 0.1 µg subcutan | 298 ± (?) | 8 | VCs control, $p < 0.05$ |
| 1 µg subcutan | 161 ± (?) | 8 | VCs control, $p < 0.001$ |

REFERENCES

1. WO 97/08202;
2. WO 05/030246
3. WO 97/08202
4. WO 97/08202
5. WO 98/21978
6. WO 00/038535.
7. WO 05/030246
8. WO 07/126364
9. WO 07/126363
10. WO 07/126365
11. WO 2010/093324
12. Lange et al., 2003; Food-induced antisecretory factor activity is correlated with small bowel length in patients with intestinal resections. APMIS. 2003 October; 111(10):985-8.
13. Laurenius et al., 2003; Antisecretory factor counteracts secretory diarrhoea of endocrine origin. Clin Nutr. 2003 December; 22(6):549-52.
14. Jennische et al., 2006; Immunohistochemical staining patterns using epitope-specific antibodies indicate conformation variants of antisecretory factor/S5a in the CNS. APMIS. 2006 July-August; 114(7-8):529-38.
15. Tomko, R. J., Jr. and M. Hochstrasser, Molecular architecture and assembly of the eukaryotic proteasome. Annu Rev Biochem, 2013. 82: p. 415-45.
16. Sixt, S. U. and B. Dahlmann, Extracellular, circulating proteasomes and ubiquitin-incidence and relevance. Biochim Biophys Acta, 2008. 1782(12): p. 817-23.
17. Johansson, E., I. Lonnroth, S. Lange, I. Jonson, E. Jennische, and C. Lonnroth, Molecular cloning and expression of a pituitary gland protein modulating intestinal fluid secretion. J Biol Chem, 1995. 270(35): p. 20615-20.
18. Bjorck, S., I. Bosaeus, E. Ek, E. Jennische, I. Lonnroth, E. Johansson, and S. Lange, Food induced stimulation of the antisecretory factor can improve symptoms in human inflammatory bowel disease: a study of a concept. Gut, 2000. 46(6): p. 824-9.
19. Lange, S. and I. Lonnroth, The antisecretory factor: synthesis, anatomical and cellular distribution, and biological action in experimental and clinical studies. Int Rev Cytol, 2001. 210: p. 39-75.
20. Johansson, E., I. Lonnroth, I. Jonson, S. Lange, and E. Jennische, Development of monoclonal antibodies for detection of Antisecretory Factor activity in human plasma. J Immunol Methods, 2009. 342(1-2): p. 64-70.
21. Johansson, E., M. Al-Olama, H. A. Hansson, S. Lange, and E. Jennische, Diet-induced antisecretory factor prevents intracranial hypertension in a dosage-dependent manner. Br J Nutr, 2013. 109(12): p. 2247-52.

22. Nilsson, S. C., R. B. Sim, S. M. Lea, V. Fremeaux-Bacchi, and A. M. Blom, Complement factor I in health and disease. Mol Immunol, 2011. 48(14): p. 1611-20.
23. Nicolas, V. and V. Lievin-Le Moal, Antisecretory peptide AF-16 inhibits the Sat toxin-stimulated transcellular and paracellular passages of fluid in cultured human enterocyte-like cells. Infect Immun, 2014.
24. Matson Dzebo, M., A. Reymer, K. Fant, P. Lincoln, B. Norden, and S. Rocha, Enhanced cellular uptake of antisecretory peptide AF-16 through proteoglycan binding. Biochemistry, 2014. 53(41): p. 6566-73.
25. DeMartino, G. N., Purification of PA700, the 19S regulatory complex of the 26S proteasome. Methods Enzymol, 2005. 398: p. 295-306.
26. Cara Polson, Pratibha Sarkar, Bev Incledon, Vanaja Raguvaran, Russell Grant. Optimization of protein precipitation based upon effectiveness of protein removal and ionization effect in liquid chromatography-tandem mass spectrometry. *Journal of Chromatography B* (2003). 785, p. 263-275.
27. Lange, S. (1982) FEMS Microbiol. Lett. 15, 239-242

The invention claimed is:

1. A pharmaceutically active salt of a peptide corresponding to a fragment of the antisecretory factor (AF) protein as shown in SEQ ID NO: 1 (AF), wherein said peptide at least comprises the amino acid sequence as shown in SEQ ID NO: 2 (AF-6) and a cysteine disulfide in amino acid (aa) position no. 1 of SEQ ID NO: 2, said peptide having antisecretory activity.

2. A pharmaceutically active salt of a peptide according to claim 1, wherein said peptide comprises the amino acid sequence as shown in SEQ ID NO: 3 (AF-16) and a cysteine disulfide in amino acid position no. 2 of SEQ ID NO: 3.

3. A pharmaceutically active salt of a peptide according to claim 1, wherein said peptide comprises the amino acid sequence as shown in SEQ ID NO:4 (AF-8) and a cysteine disulfide in amino acid position no. 2 of SEQ ID NO: 4.

4. A pharmaceutically active salt of a peptide according to claim 1, wherein the peptide consists of 6-25 amino acids, 7-17 amino acids, 7-16 amino acids, 7-20 amino acids, 8-17 amino acids, 8-20 amino acids, 17-25 amino acids, 17-20 amino acids, 7 amino acids, 8 amino acids, 16 amino acids, or 17 amino acids.

5. A pharmaceutically active salt of a peptide according to claim 1, which is at least 6 amino acids long and at the most 25 amino acids long.

6. A pharmaceutically active salt of a peptide according to claim 1, comprising the amino acids as shown in SEQ ID NO: 7 (VC(C)HSKTRSNPENNVGL), or the amino acid sequence as shown in SEQ ID NO: 8 (C(C)HSKTR), or the amino acid sequence as shown in SEQ ID NO: 9 (VC(C)HSKTR).

7. A pharmaceutically active salt of a peptide according to claim 1, consisting of the amino acids as shown in SEQ ID NO: 7 (VC(C)HSKTRSNPENNVGL), or the amino acid sequence as shown in SEQ ID NO: 8 (C(C)HSKTR), or the amino acid sequence as shown in SEQ ID NO: 9 (VC(C) HSKTR).

8. A pharmaceutically active salt of a peptide according to claim 1, which has a t½ of at least 0.2 h, 0.5 h, 1 h, or 1.5 h.

9. A pharmaceutically active salt of a peptide according to claim 8, which has a t½ of at least 1.8 h.

10. A pharmaceutical composition comprising a pharmaceutically active salt of a peptide according to claim 1 and a suitable pharmaceutical carrier.

11. A method comprising administering a pharmaceutically active salt of a peptide according to claim 1 to a patient.

* * * * *